United States Patent
Desroches

(10) Patent No.: US 10,376,158 B2
(45) Date of Patent: Aug. 13, 2019

(54) SYSTEMS AND METHODS FOR CONTROLLING AN INTERACTIVE WORKSTATION BASED ON BIOMETRIC INPUT

(71) Applicant: Sparx Smartpods Inc., Moncton (CA)

(72) Inventor: Leon Desroches, Moncton (CA)

(73) Assignee: Sparx Smartpods Inc., Moncton, New Brunswick (CA)

( * ) Notice: Subject to any disclaimer, the term of this patent is extended or adjusted under 35 U.S.C. 154(b) by 280 days.

(21) Appl. No.: 15/349,466

(22) Filed: Nov. 11, 2016

(65) Prior Publication Data

US 2017/0135587 A1 May 18, 2017

Related U.S. Application Data

(60) Provisional application No. 62/254,941, filed on Nov. 13, 2015.

(30) Foreign Application Priority Data

Nov. 10, 2016 (WO) ................ PCT/CA2016/051310

(51) Int. Cl.
*A61B 5/0205* (2006.01)
*A47B 9/20* (2006.01)
(Continued)

(52) U.S. Cl.
CPC .............. *A61B 5/0205* (2013.01); *A47B 9/00* (2013.01); *A47B 9/20* (2013.01); *A47B 11/00* (2013.01);
(Continued)

(58) Field of Classification Search
CPC ....... A47B 21/02; A47B 13/081; A47B 21/06; A47B 9/20; A47B 2083/025;
(Continued)

(56) References Cited

U.S. PATENT DOCUMENTS

| | | |
|---|---|---|
| 4,134,614 A | 1/1979 | Fielding, Sr. |
| 4,762,072 A | 8/1988 | Boundy |

(Continued)

FOREIGN PATENT DOCUMENTS

| | | |
|---|---|---|
| CA | 2840979 A1 | 10/2013 |
| CN | 201278932 | 7/2009 |

(Continued)

OTHER PUBLICATIONS

Herman Miller, Envelop Desk, http://www.hermanmiller.com/content/dam/hermanmiller/documents/product_literature/brochures/Envelop_Desk_brochure.pdf, undated [Accessed: Aug. 13, 2013].

(Continued)

*Primary Examiner* — Jonathan Han
(74) *Attorney, Agent, or Firm* — Fish & Richardson P.C.

(57) ABSTRACT

Systems and methods are disclosed for moving a tabletop of a workstation based on biometric input associated with a user, the method being performed by a controller that is configured to send control signals to actuators to move the tabletop. One method includes: accessing a user profile associated with a user device; determining parameters for moving the tabletop, based on the user profile, for eliciting desired biometric inputs from the workstation user at one or more times during the movement of the tabletop; and repeating one or more iterations of: moving the tabletop based on the parameters, by sending control signals to the actuators of the tabletop; receiving, into a data storage device, actual biometric inputs from the workstation user; comparing the received actual biometric inputs with the desired biometric inputs; and if the parameters do not elicit the desired biometric inputs, adjusting the parameters.

22 Claims, 10 Drawing Sheets

(51) Int. Cl.
| | | |
|---|---|---|
| *A47B 21/03* | (2006.01) | |
| *A61B 5/024* | (2006.01) | |
| *A61B 5/1455* | (2006.01) | |
| *A47B 11/00* | (2006.01) | |
| *A47B 13/08* | (2006.01) | |
| *A47B 21/02* | (2006.01) | |
| *A47B 21/04* | (2006.01) | |
| *A61B 5/01* | (2006.01) | |
| *A61B 5/021* | (2006.01) | |
| *A61B 5/145* | (2006.01) | |
| *A61B 5/00* | (2006.01) | |
| *A47B 9/00* | (2006.01) | |
| *G16H 20/30* | (2018.01) | |
| *G05B 15/02* | (2006.01) | |
| *A61B 5/11* | (2006.01) | |

(52) U.S. Cl.
CPC ............ *A47B 13/081* (2013.01); *A47B 21/02* (2013.01); *A47B 21/0314* (2013.01); *A47B 21/04* (2013.01); *A61B 5/01* (2013.01); *A61B 5/021* (2013.01); *A61B 5/02055* (2013.01); *A61B 5/02438* (2013.01); *A61B 5/14532* (2013.01); *A61B 5/14551* (2013.01); *A61B 5/6892* (2013.01); *G16H 20/30* (2018.01); *A47B 2200/0052* (2013.01); *A47B 2200/0059* (2013.01); *A47B 2200/0061* (2013.01); *A47B 2200/0062* (2013.01); *A47B 2200/0066* (2013.01); *A47B 2220/0097* (2013.01); *A61B 5/1116* (2013.01); *A61B 5/1118* (2013.01); *G05B 15/02* (2013.01); *G05B 2219/24162* (2013.01)

(58) Field of Classification Search
CPC .... A47B 2200/0061; A47B 2200/0062; A47B 9/00; A47B 11/00; A47B 17/02; A47B 21/03; A47B 2200/0054; A47B 2200/0056; A47B 21/0314; A47B 2200/0052; A47B 2200/0059
USPC .................. 108/20, 50.02; 700/275
See application file for complete search history.

(56) References Cited

U.S. PATENT DOCUMENTS

| | | | |
|---|---|---|---|
| 4,852,500 A | 8/1989 | Ryburg | |
| 4,880,270 A | 11/1989 | Cooper | |
| 5,323,695 A | 6/1994 | Borgman | |
| 5,909,934 A | 6/1999 | McGraw | |
| 5,988,076 A | 11/1999 | Vander Park | |
| 6,102,476 A | 8/2000 | May | |
| 6,248,014 B1 | 6/2001 | Collier | |
| 6,269,753 B1 | 8/2001 | Roddan | |
| 6,270,157 B1 | 8/2001 | Kapushinski | |
| 6,296,408 B1 | 10/2001 | Larkin | |
| 6,354,044 B1 | 3/2002 | Lagace, Jr. | |
| 6,712,008 B1 | 3/2004 | Habenicht | |
| 6,726,276 B1 | 4/2004 | Tholkes | |
| 6,817,684 B2 | 11/2004 | Cattaneo | |
| 6,848,369 B1 | 2/2005 | King | |
| 6,960,098 B1 | 11/2005 | Tseng | |
| 7,100,517 B1 | 9/2006 | Godwin | |
| 7,134,719 B2 | 11/2006 | Moglin | |
| 7,620,667 B2 | 11/2009 | Rollin | |
| 7,640,866 B1 | 1/2010 | Schermerhorn | |
| 7,677,678 B2 | 3/2010 | Mosel | |
| 7,690,317 B2 | 4/2010 | Beck | |
| 7,762,072 B2 | 7/2010 | Critchley et al. | |
| 7,823,973 B2 | 11/2010 | Dragusin | |
| 7,887,130 B1 | 2/2011 | Zvolena | |
| 8,051,782 B2 | 11/2011 | Nethken | |
| 8,141,949 B2 | 3/2012 | Baru | |
| 8,174,379 B2 | 5/2012 | Black | |
| 8,186,281 B2 | 5/2012 | Bastian | |
| 8,678,936 B2 | 3/2014 | Lesley | |
| 8,991,320 B2 | 3/2015 | DesRoches | |
| 9,167,894 B2 | 10/2015 | DesRoches | |
| 2001/0020810 A1 | 9/2001 | Kennedy | |
| 2006/0124036 A1 | 6/2006 | Xu | |
| 2006/0241520 A1 | 10/2006 | Robertson | |
| 2008/0245279 A1* | 10/2008 | Pan | A47B 9/00 108/144.11 |
| 2009/0133609 A1 | 5/2009 | Nethken | |
| 2009/0165680 A1 | 7/2009 | Bakker | |
| 2010/0201165 A1 | 8/2010 | Dankovich | |
| 2012/0031310 A1 | 2/2012 | Jedrysik | |
| 2012/0085267 A1 | 4/2012 | Kenny | |
| 2013/0106146 A1 | 5/2013 | Leclaire | |
| 2013/0116092 A1 | 5/2013 | Martinez | |
| 2013/0331993 A1* | 12/2013 | Detsch | G05B 15/02 700/275 |
| 2014/0096706 A1* | 4/2014 | Labrosse | A47B 21/02 108/21 |
| 2014/0208986 A1* | 7/2014 | DesRoches | A47B 9/20 108/22 |
| 2016/0113389 A1 | 4/2016 | DesRoches et al. | |

FOREIGN PATENT DOCUMENTS

| | | |
|---|---|---|
| EP | 1364596 | 11/2003 |
| WO | WO 2009064246 | 5/2009 |
| WO | WO 2010127425 | 11/2010 |

OTHER PUBLICATIONS

International Search Report and Written Opinion in PCT/CA2016-051310 dated Jan. 17, 2017.

The International Search Report and Written Opinion, as received in connection to international patent application PCT/CA2014/000045 dated Apr. 29, 2014.

* cited by examiner

USER PROFILE

♡ MUSCULOSKELETAL INJURIES

DO YOU HAVE ANY OF THE FOLLOWING HEALTH CONDITIONS?

|  | YES | NO |
|---|---|---|
| HERNIATED DISK LOWER BACK | ○ | ○ |
| HERNIATED DISK LOWER NECK | ○ | ○ |
| CARPAL TUNNEL | ○ | ○ |
| TENNIS ELBOW | ○ | ○ |
| PLANTAR FACIITIS | ⊘ | ○ |
| GOLFERS ELBOW | ○ | ○ |
| THORACIC OUTLET SYNDROME | ○ | ○ |
| OTHERS | ○ | ○ |

ARE YOU CURRENTLY BEING TREATED FOR THIS PRE-EXISTING HEALTH CONDITION BY A HEALTH PROFESSIONAL?

YES ⊘  NO ○

IF YES, PLEASE SELECT ONE OR ALL [PHYSIOTHERAPIST ▾]

PLEASE KEEP MY HEALTH PROFESSIONAL UPDATED ON MY CURRENT HEALTH STATUS.

YES ⊘  NO ○

[PHYSIOTHERAPIST ▾]

PHYSIOTHERAPIST
NAME
EMAIL
CLINIC
ADDRESS
TELEPHONE
CELL

[CLOSE]    [SAVE]

FIG. 7A

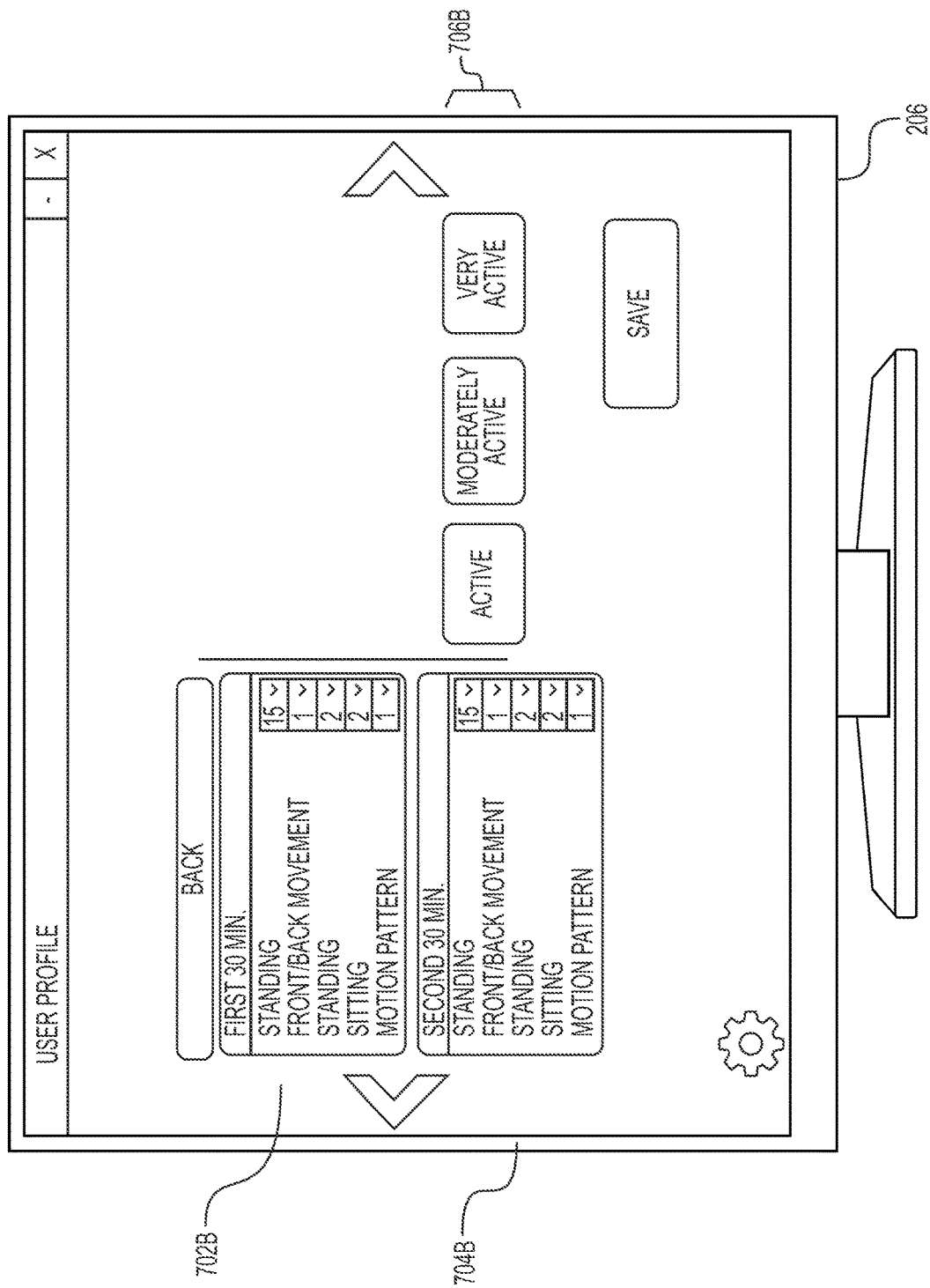

SYSTEMS AND METHODS FOR CONTROLLING AN INTERACTIVE WORKSTATION BASED ON BIOMETRIC INPUT

RELATED APPLICATION(S)

This application claims priority to U.S. Provisional Application No. 62/254,941, filed Nov. 13, 2015, and Patent Cooperation Treaty Application PCT/CA2016/051310, filed Nov. 10, 2016, disclosures of which are hereby incorporated herein by reference in their entirety.

FIELD OF DISCLOSURE

The present disclosure relates generally to the field of office workstations and, more particularly, to interactive workstations.

BACKGROUND

Seated work in a climate controlled environment may be viewed as preferable to physically intense work. Work stations tend to be designed to minimize movement and conserve energy. However, sedentary work environments may contribute to increased rates of obesity, diabetes, cardiovascular disease, high cholesterol, and musculoskeletal injuries such as carpal tunnel syndrome and degenerative disks. Each of these maladies can lead to decreased productivity, lower employee morale, and increased health care costs.

Much of the workforce in developed countries works seated at a computer. However, sitting burns fewer calories than standing which may contribute to increased rates of obesity, mortality, and in particular cardiovascular disease mortality. The World Health Organization has associated increased obesity with rising rates of type II diabetes, hypertension, stroke, sleep apnea, cholelithiasis, degenerative arthritis and certain cancers (e.g. colon cancer).

While the etiology of obesity can be complex, it may generally occur when daily energy intake exceeds total daily energy expenditure (TDEE). Human TDEE may be subdivided into three components: basal metabolic rate (BMR), thermic effects of food (TEF) and activity thermogenesis (AT). BMR is the energy required for core body function during rest, which may account for approximately 60% of a sedentary individual's daily energy expenditure. TEF is the energy required during digestion, absorption, and fuel storage after a meal, which may account for approximately 10% of a sedentary individual's daily energy expenditure. AT can be further subdivided into exercise AT (i.e. bodily exertion for the sake of developing and maintaining physical fitness), and non-exercise AT (NEAT) (i.e. energy expenditure that occurs while performing routine daily activities such as, for example, climbing stairs at home and walking in the office). Increasing an individual's AT may help reduce the risk of obesity and related maladies.

Some studies suggest that people who are predominantly seated while working (e.g. bus drivers and telephone operators), may have twice the chance of developing cardiovascular diseases (CVD) as compared to people who are able to stand throughout the day such as bus conductors or mail carriers. In fact, it has been reported that an individual's risk of suffering from metabolic syndrome as well as uncontrolled metabolic risk factors (e.g. CVD, types II diabetes, high blood pressure, unhealthy cholesterol levels, unhealthy plasma glucose levels, unhealthy plasma triglycerides levels, central adiposity, and large waist girth) may be directly related to the time the individual has spent sitting and inversely related to the individual's NEAT level.

Standing and transitioning from sitting to standing regularly may provide significant health benefits. Some studies have found that increases in muscle activity in the quadriceps during standing, as well the transition from sitting to standing, may affect specific cellular signals and regulate health risk factors, possibly better than intense exercise activities like running 35 miles/week or taking hour-long brisk walks 5 days/week. Workers who stand on a regular basis (e.g. a shop assistant) may expend up to 1400 kcal/day without engaging in any strenuous physical activity. In contrast, workers who are chair-bound may expend as little as 300 kcal/day.

Lower back pain is a common problem among seated workers. Some studies suggest that prolonged static sitting and reduced lumbar lordosis may be two significant risk factors associated with occupational lower back pain. It has been reported that workers with jobs that require prolonged sitting may be 3.2 times more likely to develop lower back pain within the first year of employment.

Some manufacturers have introduced walking workstations and cycling workstations to address the problems of sedentary workplaces. However, some studies suggest that these workstations may contribute to reduced productivity relative to standing or seated workstations.

In addition, users of workstations that enable users to move (e.g., walking workstations, cycling workstations, etc.) may not be as inclined to undergo movement for the betterment of their health due to idleness, inertia, or forgetfulness while working. Furthermore, the movements that accompany the above described workstations may not be tailored to the user's specific needs. There is thus a desire for a system and method of moving workstations that are automatic and user-specific.

SUMMARY

According to certain aspects of the present disclosure, systems and methods are disclosed for moving a tabletop of a workstation in a plurality of dimensions relative to a user position based on biometric input.

In one embodiment, a method is described for moving a tabletop of a workstation in a plurality of dimensions based on biometric input associated with the user, the method being performed by a controller that is configured to send control signals to one or more actuators to move the tabletop, wherein the controller is connected to one or more user devices having a user interface. The method may include: detecting a connection to one or more user devices having a user interface; detecting a connection to the one or more actuators of the workstation; accessing a user profile associated with or stored in a user device of the one or more user devices; determining one or more parameters for moving the tabletop, based on the user profile, for eliciting one or more desired biometric inputs from the user that indicate the health of the user or movement by the user at one or more times during the movement of the tabletop; and repeating one or more iterations of: moving the tabletop based on the one or more parameters, by sending control signals from the controller to the one or more actuators of the tabletop; receiving, into a data storage device, one or more actual biometric inputs from the user indicating the health of the user or movement by the user; determining whether the one or more parameters for moving the tabletop elicit the one or more desired biometric inputs by comparing the received one or more actual biometric inputs with the one or more desired biometric inputs; and if one or more parameters do not elicit the one or more desired biometric inputs, adjusting the one or more parameters.

In accordance with another embodiment, a system is disclosed for moving a tabletop of a workstation in a plurality of dimensions based on biometric input associated with a user. The system comprises: a data storage device storing biometric input and instructions for moving the tabletop of the workstation in the plurality of dimensions based on the biometric input; one or more user devices having a user interface enabling a user of the system to create or access a user profile; the workstation having the tabletop and at least one or more actuators that can move the tabletop; a controller having at least one processor configured to execute the instructions to perform a method including: detecting a connection to the one or more user devices; detecting a connection to the one or more actuators; accessing the user profile associated with or stored in a user device of the one or more user devices; determining one or more parameters for moving the tabletop, based on the user profile, for eliciting one or more desired biometric inputs from the user that indicate the health of the user or movement by the user at one or more times during the movement of the tabletop; and repeating one or more iterations of: moving the tabletop based on the one or more parameters, by sending control signals from the controller to the one or more actuators of the tabletop; receiving, into the data storage device, one or more actual biometric inputs from the user indicating the health of the user or movement by the user; determining whether the one or more parameters for moving the tabletop elicit the one or more desired biometric inputs by comparing the received one or more actual biometric inputs with the one or more desired biometric inputs; and if one or more parameters do not elicit the one or more desired biometric inputs, adjusting the one or more parameters.

In accordance with another embodiment, a non-transitory machine-readable medium is disclosed that stores instructions that, when executed by a processor, cause the processor to perform a method for moving a tabletop of a workstation in a plurality of dimensions relative to a workstation user position, based on biometric input associated with the workstation user. The method includes: detecting a connection to one or more user devices having a user interface; detecting a connection to one or more actuators of the workstation; accessing a user profile associated with or stored in a user device of the one or more user devices; determining one or more parameters for moving the tabletop, based on the user profile, for eliciting one or more desired biometric inputs from the workstation user that indicate the health of the workstation user or movement by the workstation user at one or more times during the movement of the tabletop; and repeating one or more iterations of: moving the tabletop based on the one or more parameters, by sending control signals to the one or more actuators of the tabletop; receiving, into a data storage device, one or more biometric inputs from the workstation user indicating the health of the workstation user or movement by the workstation user; determining whether the parameters for moving the tabletop elicit the desired biometric inputs by comparing the received biometric inputs with the desired biometric inputs; and if one or more parameters do not elicit the desired biometric inputs, adjusting the one or more parameters.

Additional objects and advantages of the disclosed embodiments will be set forth in part in the description that follows, and in part will be apparent from the description, or may be learned by practice of the disclosed embodiments. The objects and advantages on the disclosed embodiments will be realized and attained by means of the elements and combinations particularly pointed out in the appended claims.

It is to be understood that both the foregoing general description and the following detailed description are exemplary and explanatory only and are not restrictive of the detailed embodiments, as claimed.

BRIEF DESCRIPTION OF THE DRAWINGS

FIGS. 7A-7D depict various screenshots of user interfaces of the interactive workstation, in accordance with non-limiting embodiments.

DETAILED DESCRIPTION

Various non-limiting embodiments of the present disclosure will now be described to provide an overall understanding of the principles of the structure, function, and use of systems and methods disclosed herein for controlling an interactive workstation based on biometric input.

It has been determined that the risk of developing lower back pain may be reduced by regular thoracic and lumbar spinal rotation, which may increase joint mobility throughout the spine thus allowing for the hydration of intervertebral discs and improving joint nutrition. At least one embodiment of the present disclosure describes an interactive workstation that automatically utilizes a rotatable portion to rotate a tabletop with respect to a user. The interactive workstation may undergo such movements, if, for example, a user has a pre-existing health condition that can be alleviated through regular thoracic and lumbar spinal rotation.

Furthermore, some studies suggest that workers tend not to alternate between standing and sitting often enough to relieve static musculoskeletal loading. At least one embodiment described herein enables users to interact with a workstation having a controller that operates a height adjuster for automatically alternating a tabletop between a seated height and a standing height so that the user of the interactive workstation moves from a sitting position to a standing position and vice-versa at a predefined periodicity of movement that is set for the user when the user is using the workstation.

Even further, workers may often be hesitant or lack initiative to interact with the above-mentioned workstations to undergo the kinds of movements that would improve the workers' health and/or lifestyle. In some scenarios, a user may have specific health conditions and/or needs, for which a specific regimen of body movements may be required (e.g., sitting, standing, rotating the torso, etc.) at specific periodicities. At least one embodiment described herein enables users to interact with a workstation by inputting their specific health conditions and/or needs, and/or by feeding real-time data via biometric sensors that may cause the workstation to react to and/or configure various parameters of a session.

One or more examples of these non-limiting embodiments are described in detail with reference made to FIGS. 1A-1B, 2-6, and 7A-7D in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Figure 1B:
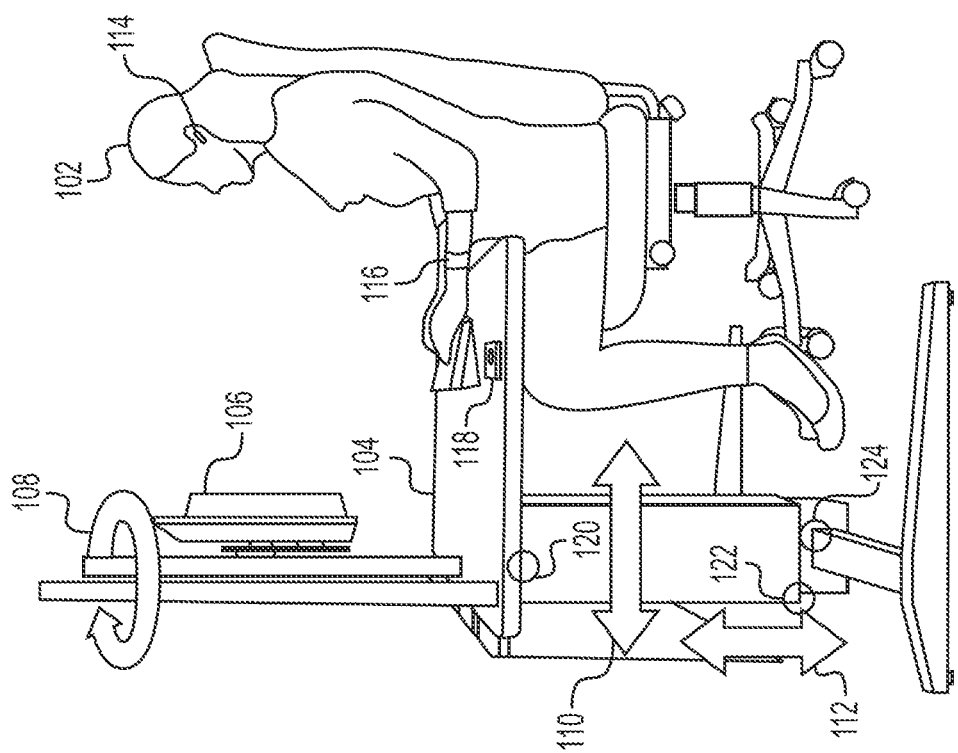
FIGS. 1A and 1B depict interactive workstations, in accordance with non-limiting embodiments.
Figure 1A:
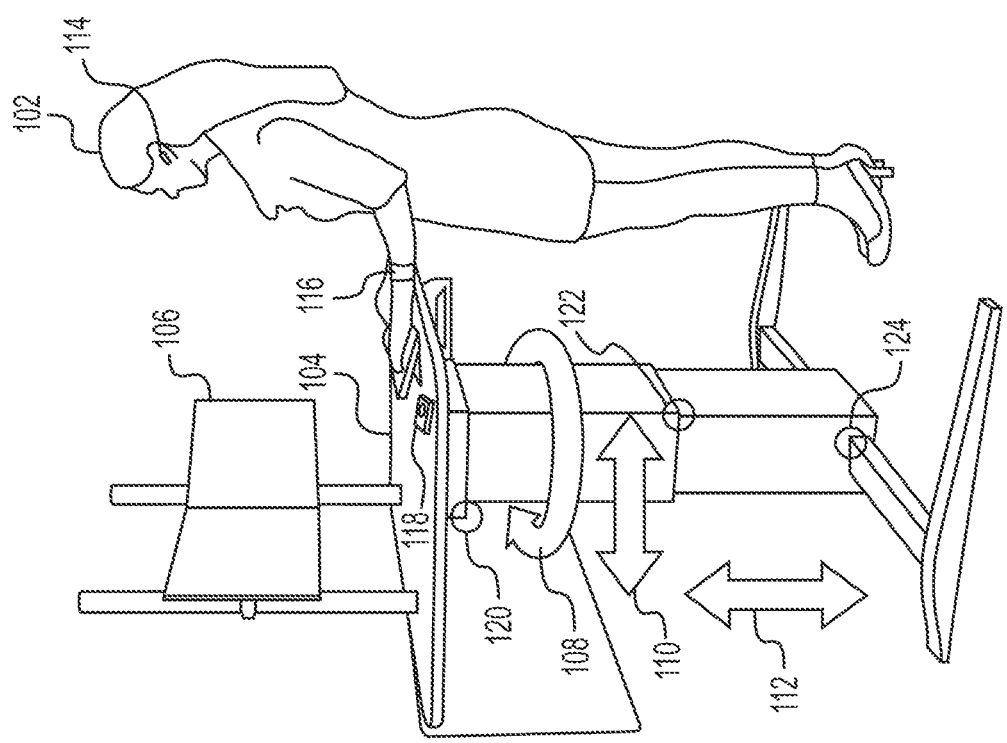

FIGS. 1A and 1B depict an interactive workstation 104 in different positions. In various embodiments an "interactive workstation" (or "workstation") may refer, for example, to a desk, table, and/or station having a tabletop where a user may work and/or otherwise be involved in an activity that may occupy the user's attention, and where various motility-inducing components coupled to the workstation (e.g., motors, adjustors, levers, rotators, etc.) may cause the tabletop to move with respect to the user, and wherein such motility-inducing components (collectively referred to as "actuators") may be directly or remotely controlled by a controller (to be described below) of the interactive workstation. As will be described in more detail in connection with FIG. 2, the controller may be one or more of a remote server accessible over a cloud network, an electronic device wirelessly and/or directly connected to the interactive workstation, or, in certain embodiments, a part of a user device 106 that may be used by the user 102 at the interactive workstation 104. A user 102 may be able to control the interactive workstation via the controller, for example, by accessing a website or running a program on the user device 106. In various embodiments, the software (e.g., a website and/or application on a user device) used to control the interactive workstation 104 via the controller may be referred to as "interactive workstation software."

In general, various embodiments of the present disclosure may allow a user 102 of the interactive workstation 104 to perform their day to day duties while the interactive workstation 104 adjusts its position (e.g., by moving up and down 112, forward and backward 110, rotating and/or pivoting 108, etc.), to achieve certain movements with respect to the user position. In some embodiments, the interactive workstation 104 may move in other directions (e.g., side to side, tilting, etc.) The movements of the interactive workstation 104 may be designed so that the interactive workstation 104 does not significantly distract the user from any tasks that the user may be performing at the workstation. Thus, due to the movements of the interactive workstation 104, a user at the interactive workstation 104 may be standing up (e.g., as in FIG. 1A), or sitting down (e.g., as in FIG. 1B), at a given time during a session. In addition, movements of the interactive workstation 104 may prompt the user 102 to step forward or backward, rotate, or step side to side during a session. The movements of the interactive workstation 104 may be designed so that they appropriately improve the health and/or well-being of the user 102.

Movements of the interactive workstation 104 may be generated by one or more actuators (e.g., 120, 122, 124 shown schematically in FIGS. 1A and 1B), which may be coupled to the interactive workstation. The interactive workstation described herein may include any of the components disclosed in U.S. Pat. No. 8,991,320 titled "Workstation having automated and powered height, depth, and rotational adjusters," or its continuation-in-part U.S. Pat. No. 9,167,894, which are both incorporated by reference herein. In some embodiments, the movements of the interactive workstation may be based, for example, on one-time, periodic, continuous, and/or real-time measurements being taken from the user 102 via biometric sensors ("sensors") 114 and 116. The biometric sensors 114 and 116 may include, for example, an ear piece 114 that measures a user's body temperature, or a wristband 116 that has an accelerometer to track the user's movement. The biometric sensors may also include stand alone or external devices (e.g., blood pressure cuff, mats, etc.). A set of movements during a prescribed time may constitute a session ("session"), which may be based on, for example, predefined parameters of the user profile associated with the user that is using the interactive workstation. In various embodiments, "parameters" may include at least one of periodicity, speed, range, duration, and types of motion for the tabletop of the interactive workstation, with respect to a user position, or a stationary reference point (e.g., on the floor). In some embodiments, the parameters of a session may be determined and/or reconfigured by the user 102. In other embodiments, the parameters may be adjusted periodically, continuously, or in real-time, based on biometric measurements taken from the user 102.

In various embodiments, a user may refer to not only the individual that undergoes movements during a session at the interactive workstation but also anyone that is engaged with the interactive workstation. For example, a user may be one or more of a health professional (e.g., doctor, therapist, medical personnel, acupuncturist, etc.), an insurance case worker, an employer, a colleague, or a manager, who would like to prescribe certain parameters of a session, for example, to treat a medical condition of the individual ("patient-user") that is working at the interactive workstation 104. The session may be programmed and/or configured at a user device 106. As depicted in FIGS. 1A and 1B,the user device 106 (e.g., the user's work computer, mobile device, a smart phone, a cell phone, a tablet, a personal digital assistant, and the like) may be situated at the workstation 104. Thus, a user 102 may be able to control the interactive workstation (e.g., accessing the interactive workstation software, programing and/or configuring a session, etc.) by interacting with the user interface of his or her user device 106 (e.g., a work computer) at the workstation (e.g., for the user that is at the interactive workstation). However, the user device 106 for controlling the interactive workstation 104 need not be at the site of the workstation 104. In some embodiments, the user device 106 may be a remote computing system located far from the interactive workstation to be controlled. For example, a health professional (e.g., doctor, therapist, nurse, acupuncturist, etc.) may be able to use his or her own user device (e.g., a computer at the health professional's clinic or facility) to control the interactive workstation 104 that the health professional's patient may use (e.g., by configuring the parameters of a session for the patient's treatment). For purposes of disclosure, since both the health professional and the patient are engaged with the control of and/or use of the interactive workstation 104, they may both be referred to as "users" of the interactive workstation 104 (or as "health professional user" and "patient-user", respectively). In some cases, any third party that is authorized by the user at the workstation may control the interactive workstation 104. For example, a user may authorize an IT or tech support to control the interactive workstation 104. A third party may be able to control the interactive workstation, for example, by logging on to an interactive workstation software on the user device of the third party.

In an illustrative scenario, a physiotherapist of a patient that is diagnosed with a back condition, for example, may program the interactive workstation 104 of the patient to perform an appropriate session that is intended to exercise the patient in a way that treats and/or alleviates the patient's back condition. The physiotherapist may be able to program the session remotely on a computing system located at the physiotherapist's office, by accessing the software and/or site to program the interactive workstation 104. When the patient goes to work, she may be able to access the session that her physiotherapist had programmed, for example, by activating the interactive workstation software and inputting information that identifies a user profile of the patient. For example, the patient-user may use a thumb print reader 118 to identify herself and have her user device 106 access her user profile for the interactive workstation software. The session that the physiotherapist has programmed for the patient's interactive workstation 104 may cause the tabletop of the interactive workstation 104 to gradually rise, rotate, and/or move forward and backward, over the course of, for example, four hours, to encourage the patient to move while she works and to treat and/or alleviate her back condition. Thus, the session may accelerate the rehabilitation of the patient-user, increase the compliance by the patient-user, and ensure the patient-user's health progress.

In other embodiments, multiple interactive workstations may be linked as part of a network, for example, among clusters of interactive workstations in one or more offices. In such embodiments, users of one interactive workstation may be able to view information received from and/or control other interactive workstations in the network. The ability to view information received from and/or control other interactive workstations in the network may be shaped, for example, by the relationships of the interactive workstations and/or users of the interactive workstations within the network. For example, the interactive workstations of a network may have a hierarchical dynamic, where a master interactive workstation enables its user to view information received from and/or control a slave interactive workstation. Information and/or the ability to control interactive workstations may be confined within the network by using a firewall and/or by encrypting data.

Figure 2:
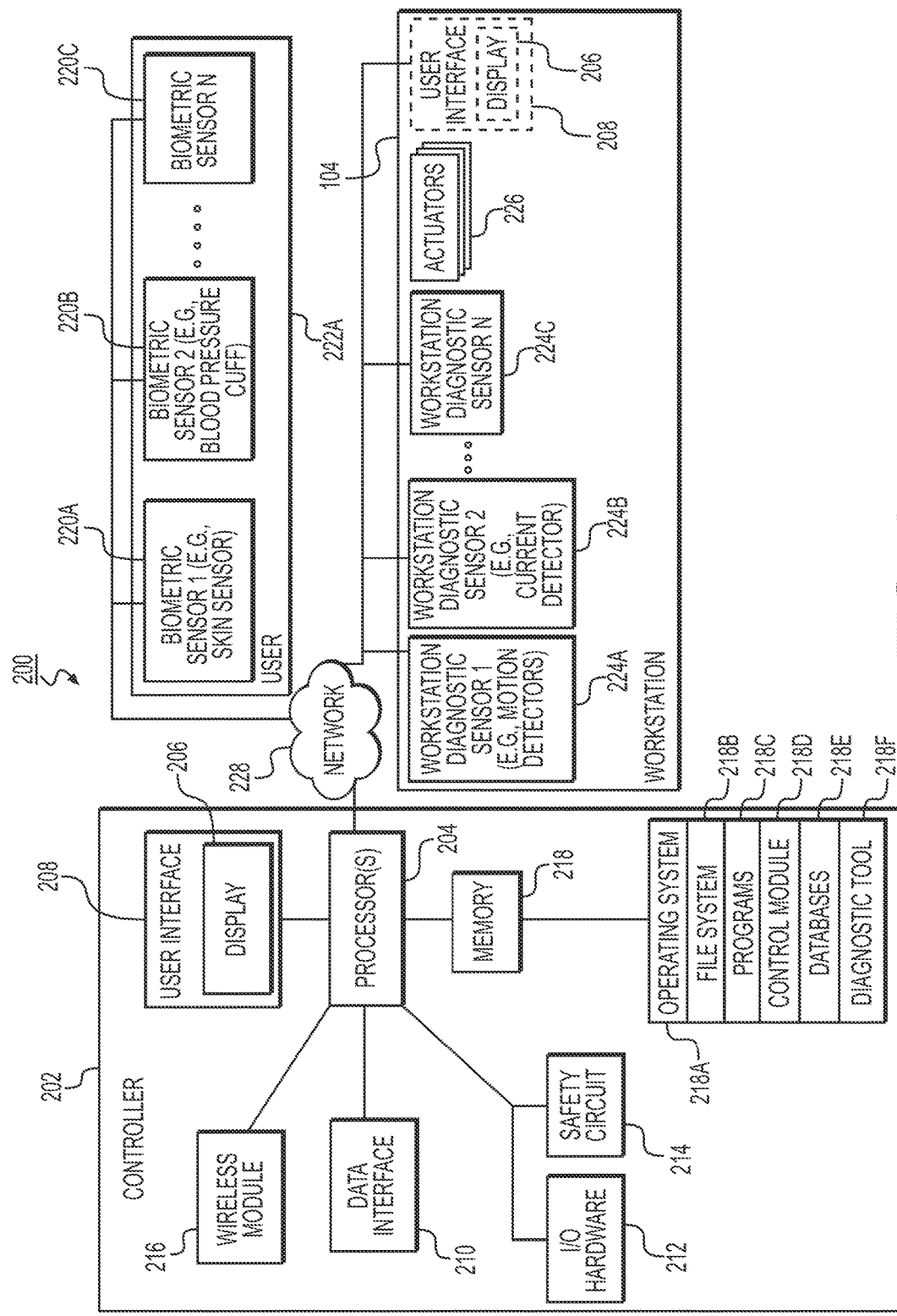
FIG. 2 depicts a block diagram of a system 200 for controlling an interactive workstation, in accordance with an exemplary embodiment.

FIG. 2 depicts a block diagram of a system 200 of the interactive workstation, in accordance with at least one embodiment. In the example shown, system 200 includes a controller 202 comprising at least one processor 204, a user interface 208 having a display 206, a data interface 210, Input/Output (I/O) hardware 212, a safety circuit 214, a wireless module 216, and a data storage device or memory ("memory") 218. System 200 further includes a plurality of biometric sensors 220A-C that may be situated on the user 222A of the interactive workstation 104 or may be standalone (e.g., a motion detector placed on the tabletop of the workstation, a blood pressure cuff shared by users of a network of interactive workstations in an office, etc.). System 200 further includes the workstation 104 comprising a plurality of workstation diagnostic sensors 224A-C and actuators 226. In some embodiments, the user interface 208 and display 206 that is being utilized by the user at the workstation may be separate from the controller 202. For example, the user interface 208 and display 206 may be a part of a user device of the user (e.g., a work computer, tablet, phone, etc.) and therefore may be located at the workstation 104. The user 222A may be able to access the controller 202 by running interactive workstation software on the user device, while the controller 202 itself may be a remote server. In some embodiments, the user device may be a desktop computer, a laptop, a mobile device, a smart phone, a cell phone, a tablet, a personal digital assistant, and the like.

The biometric sensors 220A-C may include, for example, wearable devices (e.g., wrist bands, ear pieces, skin sensors, etc.) and standalone biometric devices that may be able to connect to the controller 202 of the interactive workstation (e.g., using Bluetooth, Wifi, Zigbee, etc.) and measure or determine various biometric data (e.g., health metrics and movement metrics) of the user 222A. The standalone biometric devices may include, but are not limited to, blood pressure cuffs, or devices that can measure blood glucose, heart rate, temperature, etc.

Memory 218 includes software code for implementing one or more of an operating system 218A, a file system 218B, various programs 218C, and a database 218E. In at least one embodiment, controller 202 can be a dedicated hardware device with associated software and firmware that is configured to control the actuators 226 (e.g., a powered depth adjuster, a powered height adjuster, a powered rotator, etc.). In alternative embodiments, controller 202 can be a desktop computer, a laptop, a mobile device, a smart phone, a cell phone, a tablet, a personal digital assistant, and the like. In such embodiments, the controller 202 may be a part of the user's own computing system situated at the workstation 104.

Processor(s) 204 controls the operation of the controller 202 and can be any suitable processor depending on the configuration of the controller 202. Display 206 can be any suitable display that provides visual information depending on the configuration of the controller. For instance, display 206 can be a cathode ray tube monitor, a flat-screen monitor and the like if controller 202 is a computer. In other cases, display 206 can be a display suitable for a laptop, tablet or handheld device such as an LCD-based display and the like. In at least one embodiment, controller 202 may not include a display 206.

User interface 208 can include one or more of a mouse, a keyboard, a touch screen, a thumbwheel, a track-pad, a trackball, a card-reader, voice recognition software and the like again depending on the particular implementation of controller 202. In some cases, some of these components can be integrated with one another. For example, as shown in FIG. 2, the user interface 208 may include the display 206. In at least one embodiment, controller 202 may not include a user interface 208.

The data interface 210 can be any interface that allows the controller 202 to communicate with other devices or computers. For example, in some embodiments, there may be a network of interactive workstations 104 linked together (e.g., where each worker has their own interactive workstation 104 in an office environment). The data interface 210 may allow communication between the various interactive workstations, for example, to analyze biometric data of each user and/or to relay information among each user of the network or to a designated user. In some cases, data interface 210 can include at least one of a serial port, a parallel port or a USB port that provides USB connectivity. Data interface 210 can also include at least one of an Internet or local area network connection through an Ethernet, Firewire or modem connection or through a digital subscriber line. Various combinations of these elements can be incorporated within data interface 210.

The data interface 210 also includes elements to allow the controller 202 to communicate with the actuators 226, and can include at least one Digital to Analog converter (DAC) and at least one Analog to Digital converter (ADC). This communication includes sending control signals from the controller 202 to the actuators 226 to move the tabletop in a certain dimension at a predefined speed and periodicity of movement. In some embodiments, the controller 202 may receive information concerning the performance, functioning, and efficiency of the actuators 226 or other components of the interactive workstation from the one or more workstation diagnostic sensors 224A-C. The controller 202 may also receive information from the actuators or the tabletop such as position and speed information to keep track of the tabletop position as it is moved.

I/O hardware 212 can include one or more of a speaker, a card scanner, a camera and a printer, for example. In at least one embodiment, controller 202 does not include I/O hardware 212. Wireless module 216 is optional and can be a radio that communicates utilizing the CDMA, GSM, GPRS or Bluetooth protocol according to standards such as IEEE 802.11a, 802.11b, 802.11g or 802.11n for example. The wireless module 216 may be used to communicate and/or relay signals from the various biometric sensors 220A-C, workstation diagnostic sensors 224A-C, and/or the actuators 226 to one or more components of the controller.

Memory 218 can include RAM and flash memory elements as well as other storage elements such as disk drives and hard drives. Memory 218 is used to store one or more of operating system 218A, file system 218B and programs 218C. For instance, operating system 218A and file system 218B may provide various basic operational processes for controller 202.

Memory 218 may also store a control module 218D. Control module 218D can control the operation of the various actuators 226 based on user information received via data interface 210 for example, or data received from the various biometric sensors 220A-C and/or workstation diagnostic sensors 224A-C.

Memory 218 may also store one or more databases 218E. Databases 218E can be used to store user profile data for one or more users and/or data received from the various biometric sensors 220A-C and/or workstation diagnostic sensors 224A-C. Databases 218E can also store other information required for the operation of programs 218C or operating system 218A such as dynamically linked libraries and the like. Furthermore, the memory 218 can also store a diagnostic tool 218F and/or instructions for running a diagnostic tool 218F, for example, to manage data received from various workstation diagnostic sensors 224A-C, troubleshoot any issues related to the interactive workstation, and/or notify the user and/or third parties (e.g., a tech support team) of any performance issues.

Controller 202 may include one or more user interfaces 208. Processor(s) 204 may communicate with one or more of these user interfaces 208 to receive a user profile for a user. In alternative embodiments, processor 204 may receive a user profile through data interface 210 or wireless module 216. For instance, the user profile can be inputted by someone through user interface 208 or it can be received through data interface 210 from a user memory device (e.g. a USB storage device).

In at least one embodiment, controller 202 can be a computer that acts as a web server and provides content for a web site. One of the webpages on the website can be a webpage for configuring a user profile as described herein. In this case, a user can interact with the webpage to directly enter the information required for the processor 204 to generate and store the user profile. The user can interact with the web server and provide the required information using a desktop computer, a laptop, a tablet, a smart phone or any other suitable electronic device.

In at least one embodiment, controller 202 may be remotely controlled and/or configured (e.g., by another computer, desktop, laptop, smartphone, or tablet). For example, in embodiments where a user is a physiotherapist, medical personnel, and/or health provider, the user may remotely control and/or configure the controller 202 through a computing system that is different from the computer being used at the site of the interactive workstation by a user that is a patient of the physiotherapist, medical personnel, and/or health provider.

Controller 202 may be electrically connected, which may be done via a wired or wireless connection depending on the embodiment, to the various actuators 226 (e.g., a powered depth adjuster, a powered height adjuster, a powered rotator, etc.). During operation, the controller 202 sends control signals to the one or more actuators 226 to achieve certain movements of the tabletop with respect to the user position, according to the predefined parameters of the user profile associated with the user that is using the workstation 104, and/or according to data received by the various biometric sensors 220A-C and/or workstation diagnostic sensors 224A-C. The predefined parameters may include at least one of periodicity, speed, range, duration, and type of motion for the tabletop of the workstation 104.

Figure 3:
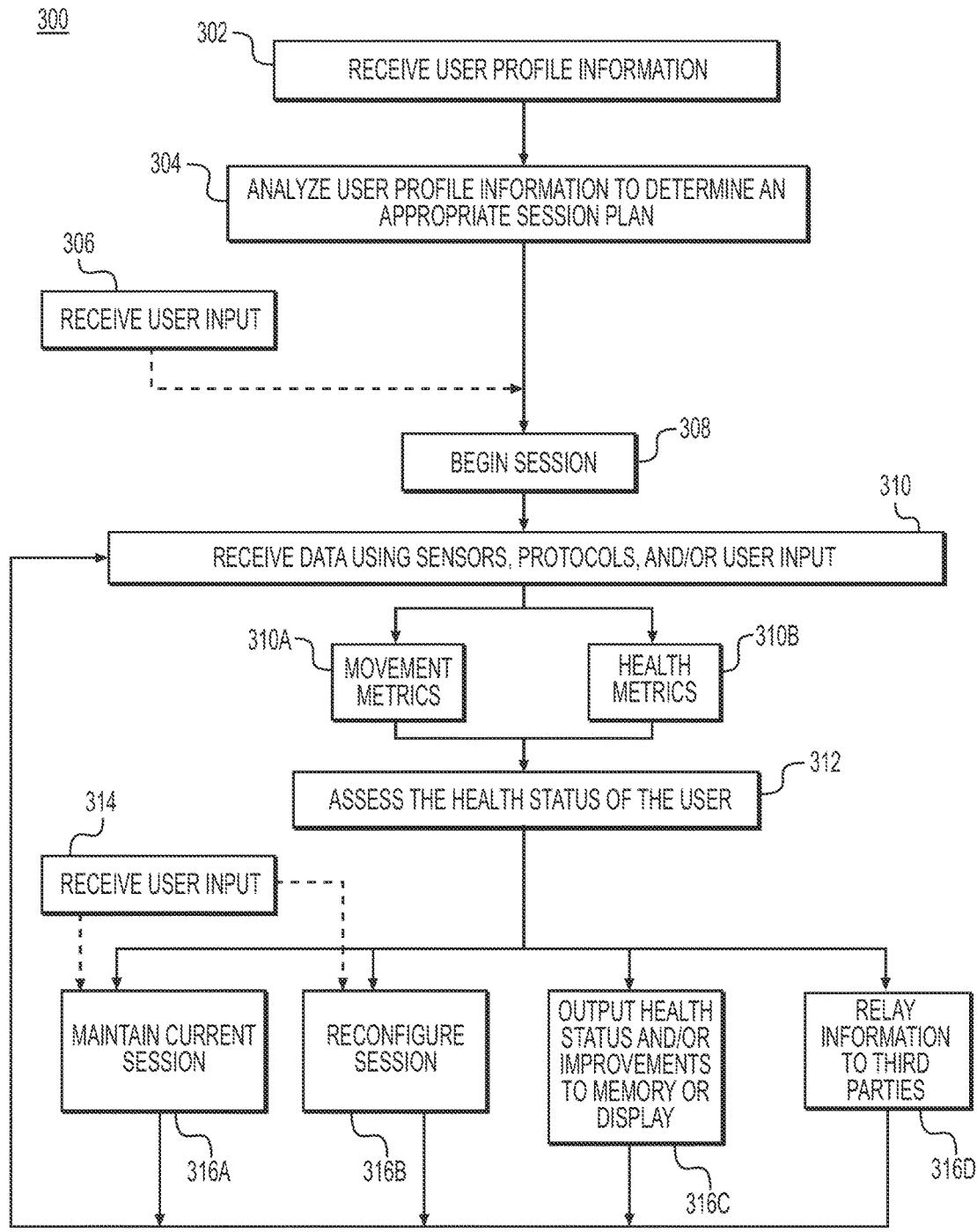
FIG. 3 depicts a flow chart of a process for interacting with a user, executed by the controller of an interactive workstation, in accordance with an exemplary embodiment.

FIG. 3 depicts a flow chart of an example process for interacting with a user 104. The process may be executed by the controller 202 of the interactive workstation 104, in accordance with non-limiting embodiments.

Figure 4:
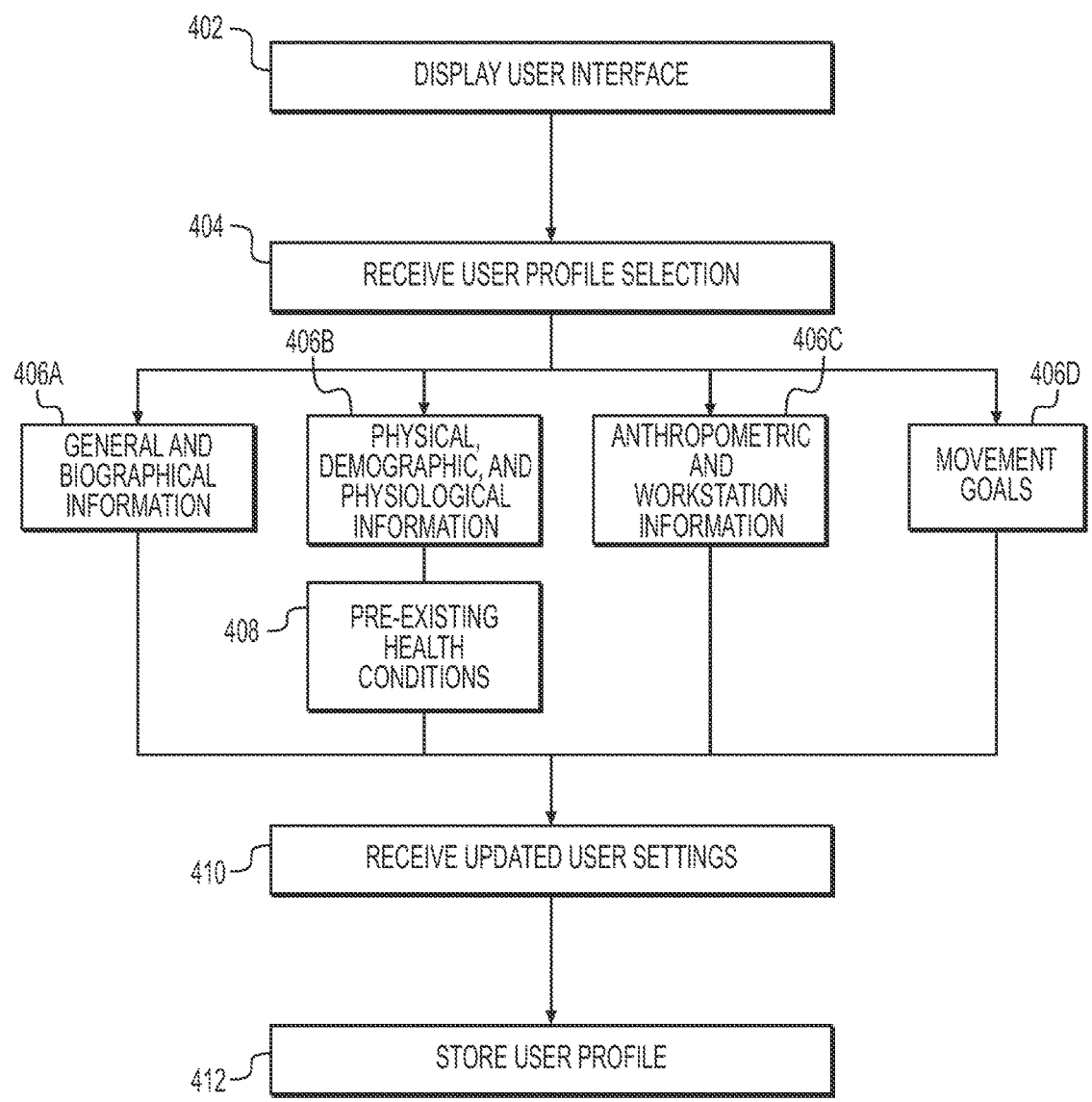
FIG. 4 depicts a flow chart of a process executed by the controller of an interactive workstation for receiving, generating, and/or updating user profile information, in accordance with an exemplary embodiment.

Step 302 may include receiving user profile information. Referring to FIG. 4, the user profile information may include one or more of: general and biographical information 406A of the user; physical, demographic, and physiological information 406B of the user; anthropometric measurements of the user and/or workstation configurations ("anthropometric and workstation measurements") 406C; and movement goals 406D of the user. The process of receiving the user profile information is explained in further detail in method 400, as described below and illustrated in FIG. 4. In some embodiments, the controller may access the user profile information from the user device. For example, a user may input information identifying the user at his or her workstation. The identifying information may be used to access and/or retrieve stored user profile information on the user device at the user's workstation. In embodiments where the controller 202 is not located at the user device at the user's workstation 104, the user device may send the user profile information to the controller 202 over a network 228. For example, a user 222A may scan his or her thumb into a thumbprint reader (or another I/O hardware 212) that is connected to a user device 106 at the user's workstation 104. Based on the thumbprint scan, the user device 106 may be able to identify the user and access his or her user profile from the interactive workstation software over a network 228.

Step 304 may include analyzing the received user profile information to determine an appropriate session plan. For example, a user's physical, demographic, and physiological information which may be received as part of the user profile information (e.g., in step 302) may be useful for determining a user's energy expenditure and for fine tuning the operational parameters of the interactive workstation 104. Likewise, a user's movement goals may dictate various parameters of the session, namely, the periodicity, type, and frequency of movement. For example, if a user's movement goal is to maximize fat burning, the parameters of a session may include a low frequency of movements, a longer period of standing, and a slower speed of those movements, since lower frequency and slower movements may be known to stimulate fat burning. In other embodiments, the interactive workstation may have a specific session tailored for a user's pre-existing health conditions. In addition, a health professional user (e.g., a doctor, physiotherapist, medical personnel, health provider etc.) may configure specific parameters to create a session designed for the patient-user. In such embodiments, the patient-user may be able to access the pre-configured session, for example, by inputting user profile information and/or by verifying the patient-user's identity.

Thus, the user profile information may be used to determine the appropriate parameters of a session plan. For example, if a user has a disc injury, the tabletop of the interactive workstation may rise at a high frequency, and have a longer period of time at a high position (e.g., to enable a user to stand longer to prevent disc compression). If a user has a stenosis (e.g., of a blood vessel), the tabletop of the interactive station may rise at a high frequency, and have a shorter period of time at a high position, since users with a stenosis may not be able to stand for long periods of time. If a user has a carpal tunnel, the tabletop of the interactive workstation may rise or descend at different heights but the movements may still be designed to maintain the user in a sitting position. The movements designed for a user with carpal tunnel may facilitate an extension of the neck (e.g., cervical spine) and thorax, and thereby increase mobility. In some embodiments, the specific adjustments in parameters may be based on a specific protocol for certain illnesses, and the protocol may be saved to the memory 218 of the controller 202.

Step 308 may include beginning the session that has been determined in step 304. It is contemplated that a user may wish to approve of and/or reconfigure the session determined in step 304 before beginning the determined and/or reconfigured session. Thus, in certain embodiments, prior the beginning the session, step 306 may include receiving a user input. Alternatively or additionally, a session may start at a preprogrammed time. A session may last any prescribed time (e.g., thirty minutes, one hour, four hours, etc.), and may constitute a set of movements based on predefined parameters, which include, for example, periodicity, speed, range, duration, and type of movements for the tabletop of the interactive workstation, with respect to user position.

Step 310 may include receiving data using sensors, protocols, and/or user input. The data may include, for example, movement metrics 310A and health metrics 310B. Movement metrics 310A may include, but are not limited to: the duration of time that the user is standing, sitting, or moving; the frequency or periodicity of a user's movement; the duration of time that the user is present or absent from the workstation; etc. Health metrics 310B of the user may include, but are not limited to: heart rate; blood pressure; respiratory rate; a measurement of oxygen saturation; glucose concentration; balance and posture; acceleration; a measurement of perspiration; body temperature; weight; caloric expenditure; and brain activity. The interactive workstation may receive measurements for movement and health metrics at any time, periodically (e.g., every five minutes) and/or continuously. Values of the various movement and health metrics may be received via user input, and/or various sensors located on the workstation (e.g., workstation diagnostic sensors) and/or the individual user (e.g., biometric sensors). Data from various sensors may be transmitted to the controller 202 over a cable (e.g., USB) or wirelessly over a network (e.g., Bluetooth, Wifi, Internet, Zigbee, etc.). In some embodiments, the data may be received via wireless module 216 of the controller 202. Furthermore, a user may also be able to input data, for example, when being prompted by the user interface 208 to provide feedback on the session so far (e.g., as in 704C in FIG. 7C).

Figure 5:
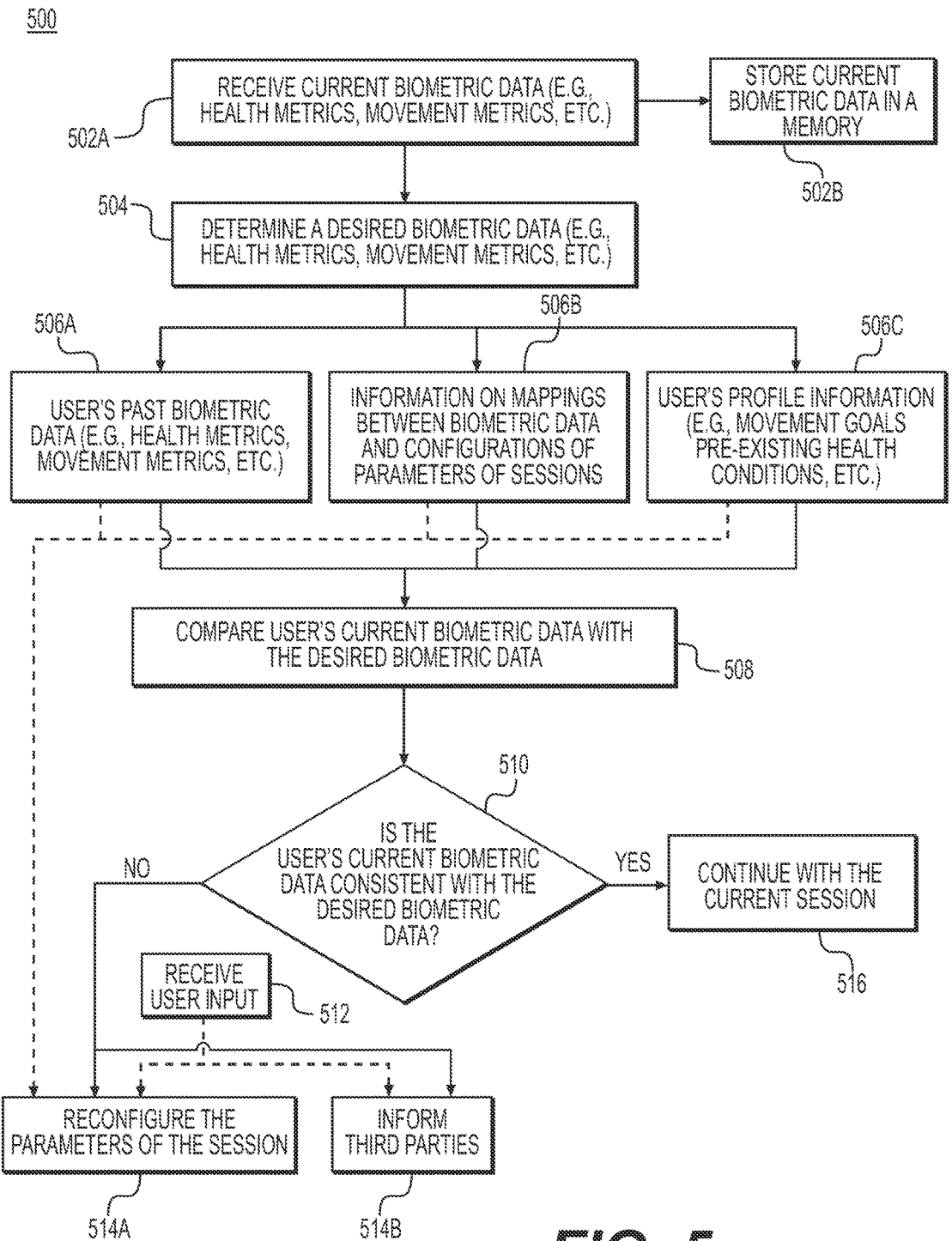
FIG. 5 depicts a flow chart of a process executed by the controller of an interactive workstation for assessing the health status of a user of the interactive workstation, in accordance with an exemplary embodiment.

Step 312 may include assessing the health status of the user based on the received data. Step 312 may include comparing the user's current received data with past data and/or data based on population studies with similar profiles as the user. For example, if the heart rate (or other health metric) of the user is below the user's typical heart rate when completing a session or part of a session with similar parameters, the assessment of step 312 may be that the user's current session may be too relaxed for the user. Method 500, as illustrated in FIG. 5, describes various embodiments of assessing the health status of the user based on received data in further detail.

Based on the assessment of step 312, one or more of the following steps (e.g., steps 316A-D) may result. Step 316A may include maintaining the current action and/or treatment session, for example, if the controller 202 of the interactive workstation 104 determines that the user's current session is appropriate for the user based on the received data. Step 316B may include reconfiguring the action and/or treatment session, for example, if the controller 202 of the interactive workstation determines that the current session is too strenuous or too relaxed for the user, based on the received data. In some embodiments, reconfiguring a session may include, for example, adjusting one or more parameters of a session (e.g., frequency, periodicity, type, speed, and range of movements of the tabletop with respect to the user), terminating a session, and/or starting a new or different session. Thus, the controller 202 of the interactive workstation 104 may monitor, evaluate, increase, or decrease movement and continue to monitor the user to reach the user's health goals and prevent injuries. In some embodiments, prior to maintaining the current action and/or treatment session, or prior to reconfiguring the action and/or treatment session, the controller 202 (via a user interface 208) may prompt the user's input (e.g., as in step 314). Receiving this user input may include displaying to the user interface 208 a reason for why a session should be reconfigured (e.g., it was too strenuous or too simple for the user) and requesting the user's approval to reconfigure. In at least one embodiment, the interactive workstation (e.g., via the controller 202) may monitor the presence of the user, and temporarily halt and/or terminate a session if the interactive workstation detects that a user is not present (e.g., via a biometric sensor 220A-C and/or workstation diagnostic sensor 224A-C). An optional pop-up may be displayed on the user interface display to alert the user that the workstation is not moving and/or that the user. In some embodiments, a user input (e.g., letting the system know that the user is back from a bathroom break) may cause the workstation to resume its session, and thereby start moving and monitoring the user again. Thus, the workstation may resume its session automatically or manually.

Step 316C may include outputting the health status and/or improvements to a memory or display. For example, a display 206 at the interactive workstation 104 may show trends and/or graphs of the values of a health metric (e.g., calories burned) over a span of time constituting the session or over several sessions. In some embodiments, users may view graphs and/or notice trends pertaining to their biometric values and/or current health. Furthermore, users may be able to track their progress using correlations and/or relationships to different statistical values. For example, users may be able to compare their received biometric data and progress to other users with similar user profile information (e.g., anthropometric information, health conditions, etc), facilitating the users to compare and/or rank themselves according to other users. In some embodiments users may be able to accumulate points and/or rewards for progressing. Furthermore, the users may be able to view the points received by other users of the interactive workstation, and thereby compete for points. In some embodiments, for example, for interactive workstations that are a part of a network, users may be able to challenge one another (e.g., one on one challenge, team challenge, multi-challenge, etc.)

Step 316D may include relaying information to third parties. Information may be sent, e.g., in the form of an email, to the user's account and/or to different recipients (e.g., health professionals, insurance caseworkers, etc.) depending on the reason for the notifications. A health professional user may choose to receive or not receive the information from their patient-users summarizing the current health status, progress and monitoring of the patient-users. The information received by a health professional user may also describe any concerning issues regarding the patient-user. For example, if the patient-user has blood pressure issues as a pre-existing health condition, the interactive workstation may create a session that is designed to make the patient-user move throughout the day to help treat and/or alleviate the patient-user's blood pressure, while continuing to monitor the patient-user's blood pressure. If, during the course of monitoring the patient-user, the patient-user's blood pressure values fluctuate significantly (high or low), the interactive workstation may, for example, send an email to a health professional with reports and/or graphs explaining any trends related to the patient-user's blood pressure. Alternatively, or additionally, the interactive workstation 104 may continue the established session and re-evaluate the patient-user's blood pressure (since movement has a direct effect on blood pressure).

Thus, the interactive workstation may inform a designated or non-designated health professional if the interactive workstation 104 detects any abnormal values of health metrics or notices any trends that may require a more detailed investigation. This may aid in preventing or alleviating biometric abnormalities (e.g., high blood pressure). In addition to health professionals, the interactive workstation 104 may also relay information about the user to insurance caseworkers, employers and/or management staff (e.g., to ensure that their employees who are users of the interactive workstation 104 are becoming healthier).

FIG. 4 depicts a flow chart of an example process 400 executed by the controller 202 of the interactive workstation for receiving, generating, and/or updating user profile information, in accordance with non-limiting embodiments. A computing device such as controller 202, or another computing device (e.g., a remote server computer, or an administrator's desktop computer) having features similar to those described above with respect to controller 202 may perform method 400.

Step 402 may include displaying a user interface display (e.g., on a display 206) of the computing device. The user interface display may correspond with software (e.g., programs 218C) stored on a memory (e.g., memory 218) of the computing device. In at least one embodiment, the user interface display may correspond with a website accessed through a data interface (e.g., data interface 210) and/or a wireless module (e.g., wireless module 216). In at least one embodiment, the user interface display may update to convey information to or request information from the user.

In at least one embodiment, the user interface display may display a prompt for credentials, such as, for example, a login and password, a biometric credential (e.g., fingerprint or facial image), a Personal Identification Number (PIN), or combinations thereof. The credentials may verify the identity of the user accessing the computing device. If the user's identity is verified and if the user has permissions to edit user settings, the method may proceed to step 404. Optionally, permission to edit user settings may be exclusive to an administrator (e.g., an office manager).

Step 404 may include the computing device receiving a user profile selection. The user profile selection may include a request to make a new profile or a selection of an existing profile. In at least one embodiment, the user interface display may display a prompt for a user profile selection. The prompt may include a list of user profiles stored in a memory (e.g., in database 218E of memory 218) of the computing device or stored elsewhere. In some embodiments, receiving a user profile selection may include reading a user device using a user device reader. A user device may be any mobile device that can store or be used to identify a particular user profile. For example, a user device may be a user ID card that includes a user ID encoded onto a magnetic strip. The user ID can be used to identify a user profile corresponding to that user ID. In this case, the user device reader may be a card reader. In another example, a user device may be a user memory device (e.g., a USB memory key or a memory card) that can store a user profile. In this case, the user device reader may be a USB interface along with a processor, or memory card reader.

In at least one embodiment, the user interface display may display a prompt requesting a user profile ID (e.g., a name or a number). The user profile ID may correspond to a user profile stored in the memory of the computing device or stored elsewhere. In at least one embodiment, receiving a user profile selection may include reading data from a user ID card (e.g., via a card scanner of I/O hardware 212). The data from the user ID card may correspond to a specific user profile, so that the computing device can interpret the data as a user profile selection.

In at least one embodiment, receiving a user profile selection may include detecting the insertion of a user memory device (e.g., a USB storage key, or a memory card such as an SD card, or a compact flash card for example) and identifying a user profile stored on the user memory device or the lack thereof. If a user profile is stored on the user memory device, then the computing device may receive the selection of that user profile upon insertion of the user memory device. If a user profile is not stored on the user memory device, then the computing device may receive a selection for a new user profile upon insertion of the user memory device.

Generally, a user profile may include a plurality of user settings. The user settings may be specific to the user to whom the user profile corresponds. In at least one embodiment, the user profile may include one or more of: general and biographical information 406A; physical, demographic, and physiological information 406B; anthropometric and workstation information 406C; and movement goals 406D. General and biographical information 406A about the user may include, for example, the user name, address, contact information, etc. The general information may also include information regarding the user's doctor, insurance provider, physiotherapist, and/or employer.

In at least one embodiment, a user profile may include physical, demographic, and physiological information 406B which may be useful for determining a user's energy expenditure and for fine tuning the operational parameters of workstation 104. The physical, demographic, and physiological information may be used to determine a user's preexisting health conditions 408. Alternatively or additionally, a user may input his or her preexisting health conditions 408 as part of creating or updating the user profile. In some embodiments, the user interface 208 may present a map or illustration of a human anatomy to the user on the display 206, and enable the user to point to a part of the human anatomy that is injured and/or where the user experiences pain.

The physical, demographic, and physiological information 406B may include one or more of height, weight, age, gender, blood pressure, glucose values, cholesterol level, and an activity level. In at least one embodiment, this information may be used to determine the individual's overall health and to set the default speed and frequency preferences. In at least one embodiment, this information may be collected regularly to track and present a user's progress on display 206. Alternatively or additionally, one or more physical, demographic, and physiological information of the user may be obtained via one or more biometric sensors 220A-C and/or workstation diagnostic sensors 224A-C.

Anthropometric and workstation information 406C may include, for example, a seat height of the chair, a user's sitting and standing elbow height, and a user's eye height (all when wearing usual footwear), minimum and maximum horizontal depth positions of tabletop, maximum rotation of the tabletop in clockwise and counterclockwise directions for each of the seated and standing positions, etc. In at least one embodiment, some of the anthropometric measurements may be calculated using body measurements of the user (e.g. forearm length, knee height, etc.). In at least one embodiment, a user profile may include workstation positions and measures such as elbow height when standing when wearing usual footwear and seated, and a horizontal depth position of the tabletop in the seated and standing positions (e.g. to maintain the user's upper arms in a relaxed position hanging down from the shoulders).

The movement goals 406D of a user may include, for example, a desired frequency of movement (e.g. "active", "moderately active", "somewhat active", or "personalized") corresponding to a periodicity of movement. For example, a workstation 104 configured to an "active" frequency of movement may rotate and change height more frequently (and possibly more quickly) than a workstation 104 configured to a "somewhat active" frequency of movement. In some embodiments, the workstation may have various preset movement goals (e.g., active, moderately active, very active, etc.) to allow for quick set-up and start. In at least one embodiment, there may be a "personalized" frequency of movement, wherein the periodicity of vertical movement and the periodicity of rotational movement may be specified independently. Furthermore, a user profile may include custom variable periodicity of movement patterns such as a standing duration and a separate seating duration as part of a personalized frequency of movement. Furthermore, these customized movement goals may be configured and/or reconfigured on a durational basis (e.g., hourly, every 30 minutes, etc.). In some embodiments, for example, where a user is a medical personnel and/or physiotherapist of a patient, rehabilitation protocols may be used to configure movement goals for a patient undergoing therapy for certain injuries, such as, but not limited to: back pain, neck pain, sciatica, herniated disc, carpal tunnel, etc.

In some embodiments, for example, when making a new profile, the interactive workstation 104 may prompt the user to view an informational video. The informational video may explain to the user, for example, how to set up a user profile, how to use the interactive workstation 104, safety benefits of the interactive workstation, and health benefits of the interactive workstation.

At step 410, the computing device may receive updated user settings. For example, the user interface display may update to prompt for one or more of: the general and biographical information 406A; physical, demographic, and physiological information 406B; anthropometric and workstation measures 406C; and movement goals 406D, as described above. In at least one embodiment, the computing device may display (e.g., on a display 206) text, images, audio or other multimedia content to provide instructions on how to determine or measure the information for the user profile. For example, the computing device may display instructions that the chair height should be measured while a seated user's thighs are approximately level with the floor while wearing usual footwear.

At step 412, the computing device may store the user profile including the updated user settings. In at least one embodiment, the computing device may store the user profile in response to input from an input device (e.g., user interface 208) such as a keyboard, mouse, or touchscreen. In the case of an existing user profile, storing the user profile may include overwriting or updating the existing user profile. In the case of a new user profile, storing the user profile may include storing the new user profile. In at least one embodiment, storing the user profile may include copying the user profile to a user memory device. In at least one embodiment, storing the user profile may include copying the user profile to or updating a user profile on a memory of the computing device, or a remote memory (e.g., a memory 218 of a controller 202 of a workstation 104, or a memory of a remote server computer).

FIG. 5 depicts a flow chart of an example method 500 executed by the controller 202 of the interactive workstation for assessing the health status of a user of the interactive workstation, in accordance with non-limiting embodiments. Method 500 explains one example of how to perform step 312, 314, and/or steps 316A-D of method 300 in further detail.

Step 502A may include receiving current data on health metrics and movement metrics ("current biometric data"). Step 504B may include storing the received current biometric data to a memory (e.g., memory 218 of controller 202). The current biometric data involve the movement metrics and health metrics described in connection with FIG. 3, and may be received by the controller 202 as previously described. Biometric data from various sensors (e.g., biometric sensors 220A-C) may be transmitted to the controller 202 over a cable (e.g., USB) or wirelessly over a network 228 (e.g., Bluetooth, Wifi, Internet, Zigbee, etc.). In some embodiments, the current biometric data may be received via the wireless module 216 of the interactive workstation. Furthermore, a user may also be able to input data, for example, when being prompted by the interactive workstation to provide feedback on the session so far (e.g., as in 704C in FIG. 7C).

Step 504 may include determining a desired biometric data (e.g., health metrics, movement metrics, etc.). The desired biometric data may be an ideal biometric data that the current configuration of parameters at the current time of the session are designed to elicit, whereas the current biometric data may be the actual biometric data received in step 502A. The desired biometric data may be based on various factors, including, but not limited to, the user's past biometric data 506A (e.g., health metrics and movement metrics that the controller received in the past), information on mappings between biometric data and the configured parameters for sessions (e.g., as in 506B), or user profile information 506C (e.g., movement goals, pre-existing health conditions, etc.).

Thus determining a desired biometric data for step 504 may include, for example, receiving a user's past data on movement metrics and/or health metrics ("past biometric data"). In some embodiments, a user's past biometric data may be retrieved from memory 218. Like the current biometric data, the past biometric data may include the movement metrics and health metrics described in connection with FIG. 3, and may be received by the controller 202 as previously described.

Determining a desired biometric data may include receiving information on mappings between biometric data and configured parameters for sessions. In some embodiments the mappings may extend to user profile information (e.g., physical, demographic, and physiological information of the user).

In one embodiment, the controller 202 may have already mapped previously received biometric data, previous configuration of parameters of past sessions, and user profile information. In such embodiments, the mappings may be saved in memory 218 for the controller 202 to retrieve. The mappings may include, for example, a determination of which types of biometric data can be predicted from a set of configured parameters of a session. The prediction may rely, for example, on a relationship between the user's past biometric data and past configurations of parameters during the corresponding sessions when biometric data was collected. For example, based on past data collected from biometric sensors of the user, the controller 202 of the interactive workstation may determine that a sequence of rapidly standing and rapidly sitting down every thirty minutes would provide a heart rate that stays at a constant value while a measurement of brain activity fluctuates in a certain predictable manner. Additionally or alternately, the prediction may rely on population data, the data of other users of the interactive workstation (e.g., in the same network as the instant user) and/or a machine learning based algorithm.

Determining a desired biometric data may also depend, for example, on the user profile information 506C (e.g., movement goals, pre-existing health conditions, etc.). For example, a debilitating illness of the user's spine may affect a user's expected biometric input, even if in past sessions, a similar set of configured parameters led to different biometric inputs. As a result of a different expectation of biometric inputs due to the debilitating illness, the desired biometric input may be different.

Step 508 may include comparing the user's current biometric data with the desired biometric data determined in step 504. For purposes of this disclosure, a "desired biometric data" may also be used, in one or more embodiments, to refer to an expected biometric data, as a result of, for example, the configured parameters of the current session, a user's past biometric data, and the user profile information.

Step 510 may include determining whether the user's current biometric data is consistent with a desired biometric data (e.g., a desired movement metric or health metric). In some embodiments, this determination may be based on an indication that certain received biometric values are not where they should be on a daily or monthly basis. In such embodiments, the determination may include comparing the user's current biometric data with the user's past biometric data. In some embodiments, the past biometric data may be in the form of data from sensors, recorded daily, weekly, and/or monthly.

If, subsequent to step 510, the user's current data is not consistent with the user's past data, the controller 202 of the interactive workstation 104 may perform one or more of steps 514A and/or 514B. Like step 314B, step 514A may include reconfiguring a session. Reconfiguring a session may include, for example, adjusting one or more parameters of a session (e.g., frequency, periodicity, type, speed, and range of movements of the tabletop with respect to the user), terminating a session, and/or starting a new or different session. In some embodiments, the particular reconfiguration may also depend on, for example, user's past biometric data (e.g., 506A), information on mappings between biometric data and configured parameters (e.g., 506B), and user profile information (e.g., 506C). For example, the information mappings combined with the desired biometric data determined in step 504 may be used to determine which configured parameters predict the desired biometric data. Furthermore, a user's movement goals and past biometric data may dictate the appropriate configurations of the parameters. For example, as described previously, based on past data collected from biometric sensors of the user, the controller 202 of the interactive workstation may determine that a sequence of standing and sitting down every thirty minutes provides fluctuations in measurements of brain activity while maintaining the heart rate of the user. Based on the desired goals of a user, for example, a desired trend for a health metric (e.g., decrease cholesterol), the controller 202 may form feature vectors comprising of, for example, favorable values of the desired health metrics (e.g., low cholesterol or a decreasing rate of cholesterol) from past data of the user or population data. The controller 202 may then associate the feature vectors with values of various parameters for sessions that may have caused the favorable health metrics (e.g., low cholesterol levels and/or decreasing rate of cholesterol). The controller 202 may then train a machine learning algorithm using the associated feature vectors to predict the parameters of a session and/or movement metrics that will lead to the favorable outcome in the health metric.

If, subsequent to step 510, the user's current data is consistent with the user's past data, step 516 may include continuing the current session. Step 516 may, in some embodiments, include maintaining the current parameters of the session.

Together, determining whether the currently received biometric data is consistent with a desired biometric data (e.g., step 510) and then prompting the controller 202 to reconfigure the parameters of a session (e.g., 514A) may be based on the input of biometric data from various sensors. For example, low accelerometer or pedometer readings (e.g., via a wearable Fitbit) may indicate that a user has not moved enough, and the controller 202 may cause the interactive workstation to increase the frequency of movements. Blood pressure and/or heart rate measurements that are lower than past blood pressure measurements during the performance of similar movements may indicate the need to reconfigure the parameters of a session to make the session more active for the user. A tilting of the user's head may indicate a sign of sleepiness, and may indicate the need for more movement. In some embodiments, certain sensors may track brain activity over time, and the controller 202 may regularly reconfigure the parameters of a session, for example, to maintain a desired level of brain activity, based on a learning which parameters triggered the desired level of brain activity in the past. Furthermore, sensors measuring cholesterol, glucose, and/or caloric burn may indicate, based on past measurements, whether the current movements of the tabletop, with respect to the user position, bring cholesterol, glucose, and/or caloric burn to desired levels. If not, the past data may be used to determine, for example, which configurations of parameters have brought the appropriate biometric to a desired level in the past. Even further, sensors related to measuring and/or evaluating a user's posture (e.g., posture tunnel) may indicate whether the current movement has a favorable effect on the user's posture. If not, past data gathered from the sensors may be used to determine which parameters of movement have led to a favorable effect on the user's posture, for example. Thus, the interactive workstation may monitor, evaluate, increase, or decrease movement and continue to monitor the user to reach the user's health goals and prevent injuries. By regularly evaluating and re-evaluating the health and/or movement metrics on a continuous and/or periodic basis (e.g., every five minutes, every thirty minutes, hourly, daily, weekly, monthly, etc.), and modifying parameters and/or recommending proposed actions, the interactive workstation may help improve a user's lifestyle and/or health, while the user may be busy working at his or her respective workstation.

Like step 316D, step 514B may including informing third parties, for example, if the current biometric data is not consistent with the desired biometric data and/or outcome. The third parties may include, but are not limited to, health professionals, physiotherapists, health insurance case researchers, employers and/or managers, etc. For example, if the interactive workstation receives any abnormal values of a health metric (e.g., a high blood pressure) as current data, as compared to a past data or a desired biometric data (e.g., healthy blood pressure range), the interactive workstation 104 may inform a health professional (e.g., by sending an email notification to the health professional).

In some embodiments, prior to reconfiguring the session (e.g., as in step 514A) or prior to informing third parties (e.g., as in step 514B), the interactive workstation 104 may prompt the user's input in step 512 (e.g., as in step 312). In some embodiments, receiving this user input may include displaying, on a display 206 of the user interface 208, a reason for why a session should be reconfigured (e.g., it was too strenuous or too simple for the user) and requesting the user's approval to reconfigure.

Figure 6:
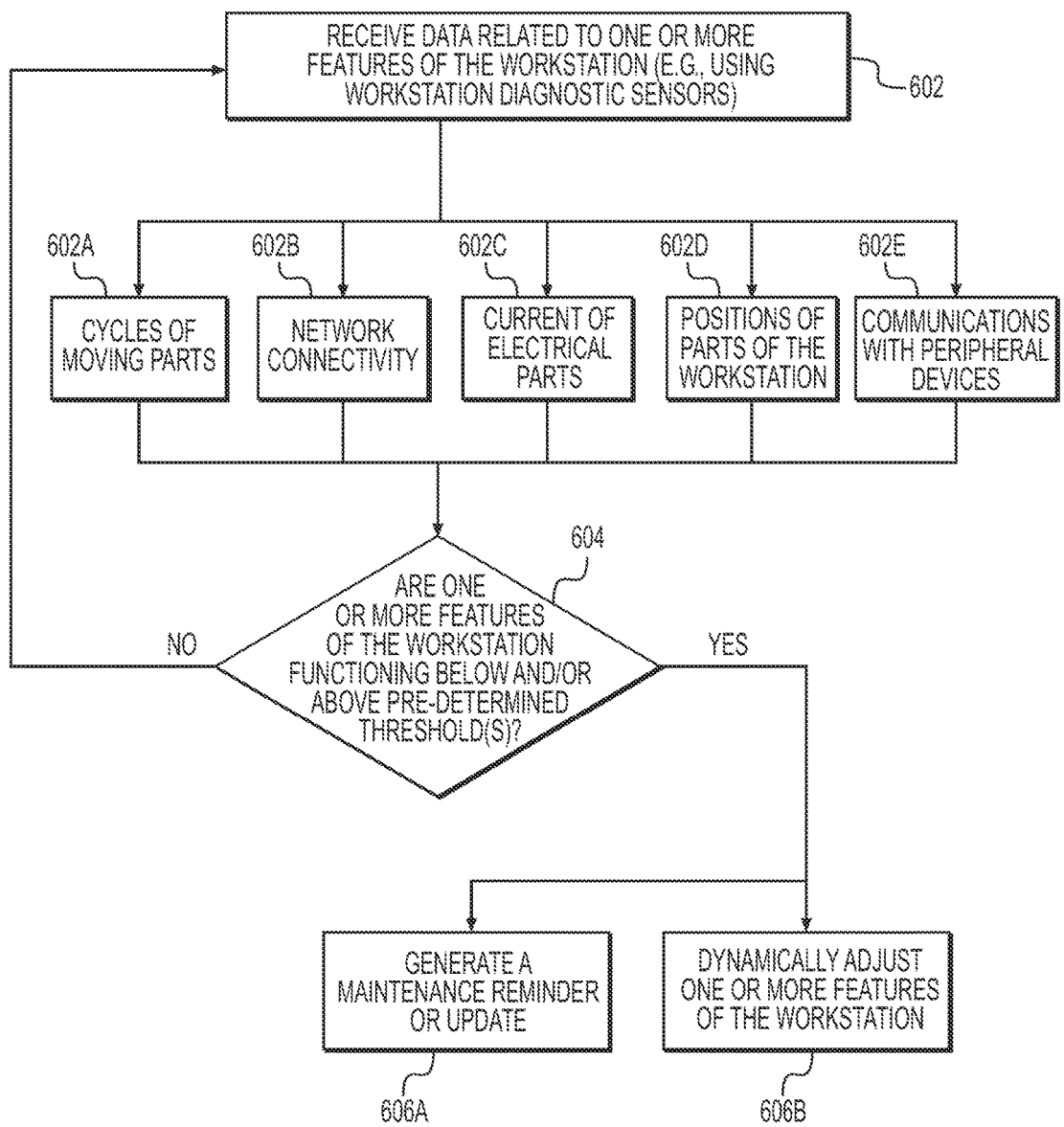
FIG. 6 depicts a flow chart of a process executed by the controller of an interactive workstation for ensuring safe and efficient operation of the interactive workstation.

FIG. 6 depicts a flow chart of an example process executed by the controller 202 of the interactive workstation 104 for ensuring safe and efficient operation of the interactive workstation 104.

Step 602 may include receiving data related to one or more features of the workstation (e.g., using workstation diagnostic sensors 224A-C). The controller 202 of the interactive workstation 104 may receive this data at any time, periodically (e.g., every five minutes) and/or continuously (e.g., in real time). Data of one or more features of the workstation may be received via the workstation diagnostic sensors 224A-C and/or user input. In some embodiments, data related to one or more workstation features may be obtained from biometric sensors 220A-C and/or from other devices located on the user's workstation (e.g., the computing system of the user). Data from the various sensors may be transmitted to the interactive workstation 104 over a cable (e.g., USB) or wirelessly over a network (e.g., Bluetooth, Wifi, Internet, Zigbee, etc.). In some embodiments, the data may be received via the wireless module of the interactive workstation. Furthermore, a user may also be able to input data, for example, when being prompted by the interactive workstation 104 to provide feedback on the session so far (e.g., as in 704C in FIG. 7C). The received data may be used by the diagnostic tool 218F of controller 202 to diagnose any issues or problems that the workstation could be experiencing for its users. This may allow the interactive workstation to diagnose any issues related to the workstation (e.g., actuators) from a distance and provide online support to the user, reconfigure the session, and/or attempt to fix the issues.

The various workstation features, for which data is received, may include one or more of, the cycles of moving parts 602A, network connectivity 602B, current of the electrical parts 602C, positions of the parts of the workstation 602D, and/or communications with peripheral devices 602E.

Step 604 may include determining whether one or more workstation features are functioning below and/or above pre-determined thresholds. For example, step 604 may include determining whether the Wifi network that facilitates communication between the various sensors and the controller 202 falls below a predetermined signal strength. The determination may be performed by a processor 204 of controller 202, using, for example, the workstation diagnostic tool 218F.

If, subsequent to step 604, one or more workstation features functions below a predetermined threshold, step 606A may include generating a maintenance reminder and/or update. For example, the interactive workstation 104 may display a window on the user interface that informs the user that one of the actuators may be malfunctioning (e.g., if a motor's speed below what it should be).

Alternatively or additionally, if one or more features of the workstation functions above and/or below a predetermined threshold, step 606B may include dynamically adjusting the one or more features of the workstation. For example, the diagnostic tool 218F of controller 202 may notify a server of the interactive workstation, enabling a distant user of the interactive workstation 104 (e.g., a troubleshooting or technical staff) to monitor the interactive workstation 104 in real time and minimize the downtime for the user that is directly experiencing problems.

While method 600 may describe at least some issues related to functionality that the interactive workstation may diagnose and/or treat, it is contemplated that the interactive workstation 104 may also be able to diagnose and treat other issues, for example, related to safety and mechanical stability. In at least some embodiments, the interactive workstation 104 may have a safety system, to prevent a blockage, compression, and/or safety hazard related to the positions of various parts of the workstation and/or actuators. The safety system may be a component of the controller 202 and may be triggered by received data related to one or more features of the workstation (e.g., as in step 602), for example, if the received data indicates a blockage, compression, and/or safety hazard related to the positions of various parts of the workstation and/or the actuators. If triggered, the safety system may cause the workstation to move in a way that stops the blockage, compression, and/or safety hazard. For example, if a workstation diagnostic sensor 224A-C detects that one of the actuators is compressing a foreign object during a movement downwards on to the foreign object, the safety system may reverse the downward movement, in order to decrease the compression on the object. The system may include a gas strut and measure current dynamically and react when values exceed the desired thresholds. The system may also calibrate itself during movement in order to prevent injury. For example, one workstation diagnostic sensor may keep track of the weight on the tabletop. If the weight on the tabletop dramatically changes when the interactive workstation performs a certain movement for instance, if books placed on the tabletop of the workstation fall over and therefore reduce the weight on the tabletop, the interactive workstation may calibrate its movement to ensure safety and/or prevent any injuries.

FIGS. 7A-7D depict various screenshots of user interfaces of the interactive workstation, in accordance with non-limiting embodiments.

For example, FIG. 7A depicts an example screenshot of a display 206 of a user interface 208 prompting the user to enter user profile information. As depicted in FIG. 7A, the display 206 shows an example questionnaire 702A that prompts the user to enter on the user interface 208, for example, preexisting musculoskeletal injuries. By receiving physical, demographic, or physiologic information (e.g., pre-existing health conditions) via user input, the interactive workstation 104 may be able to determine an appropriate session plan for the user (e.g., as in step 304 of method 300). The display 206 of the user interface 208 also prompts the user to input whether the user is undergoing treatment related to the health condition (e.g., at 704A) and whether the user desires to inform the health professional related to treatment on details regarding the session (e.g., "Please keep my health professional updated on my current health status" 706A). If the user decides to keep his or her health professional informed, the display 206 of the user interface 208 may also prompt the user to input the contact details of the health professional (e.g., at 708A).

FIG. 7B depicts an example screenshot of a display 206 of a user interface 208 once the controller 202 of the interactive workstation 104 has determined an appropriate session plan based on the user profile information (e.g., as in step 304 of method 300). As shown in FIG. 7B, the first 30 minutes of the session includes standing, front/back movement, standing, sitting, and motion pattern (e.g., at 702B). The second 30 minutes (e.g., 704B) of the session may include the same sequence of movements. As described above, in various embodiments, a user may have the option to change one or more parameters of a session, e.g., the type, frequency, periodicity, and range, of movement. For example, 706B illustrates that a user may choose to have the interactive session at a difficult (e.g., "very active"), moderate (e.g., moderately active), or normal (e.g., "active") level.

Figure 7C:
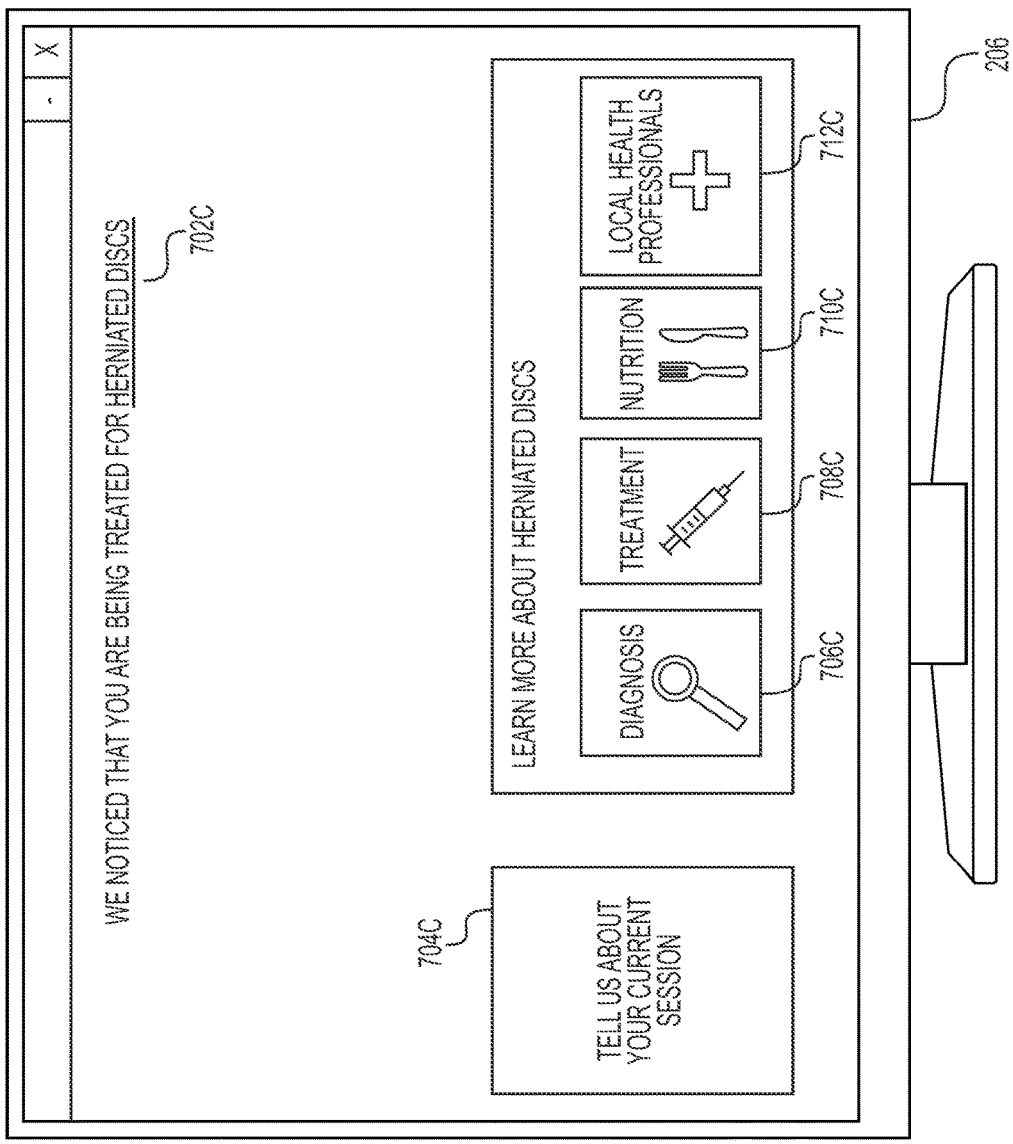

FIG. 7C depicts an example screenshot of a display 206 of a user interface 208 during a session that is designed for a user with a pre-existing health condition (e.g., herniated discs 702C). Once the interactive workstation 104 receives input from a user regarding a pre-existing health condition, determines a session plan based on the input, and begins the session, the user interface 208 may display information specific to the pre-existing health condition of the user. For example, as depicted in FIG. 7C, the user interface 208 may display information related to the diagnoses 706C, treatment 708C, and nutrition 710C for users with herniated discs. In some embodiments, the user interface 208 may even direct the user to local health professionals 712C and/or medications that treat the health condition of the user (e.g., herniated discs). The health professionals may include, e.g., medical doctors, therapists, chiropractors, masseuses, osteopathic doctors, etc. During the course of a session, for example, to treat a pre-existing health condition, the user interface 208 may enable a user to provide feedback (e.g., at 704C) on the ongoing session, for example, if the user feels that the session is too strenuous, and that their pain is increasing. In one embodiment, the user can interact with the user interface 208 at the end of a session and say that they are feeling better or worse based on a Likert Scale. As a result of receiving feedback, the controller 202 of the interactive workstation 104 may modify one or more parameters of the session and/or send a notification to a third party (e.g., health professional, therapist, caseworker, etc.).

In some embodiments, for example, where the user does not have a pre-existing health condition but is motivated to begin a session with the interactive workstation 104 for leisure needs, the user interface 208 may be able to advertise and/or direct the user to specific events, services, and/or products in the user's local area based on the user profile information of the user. In some embodiments, the controller may be able to relay various user profile information and/or biometric data of the user to social media platforms (e.g., Facebook, Google, etc.).

Figure 7D:
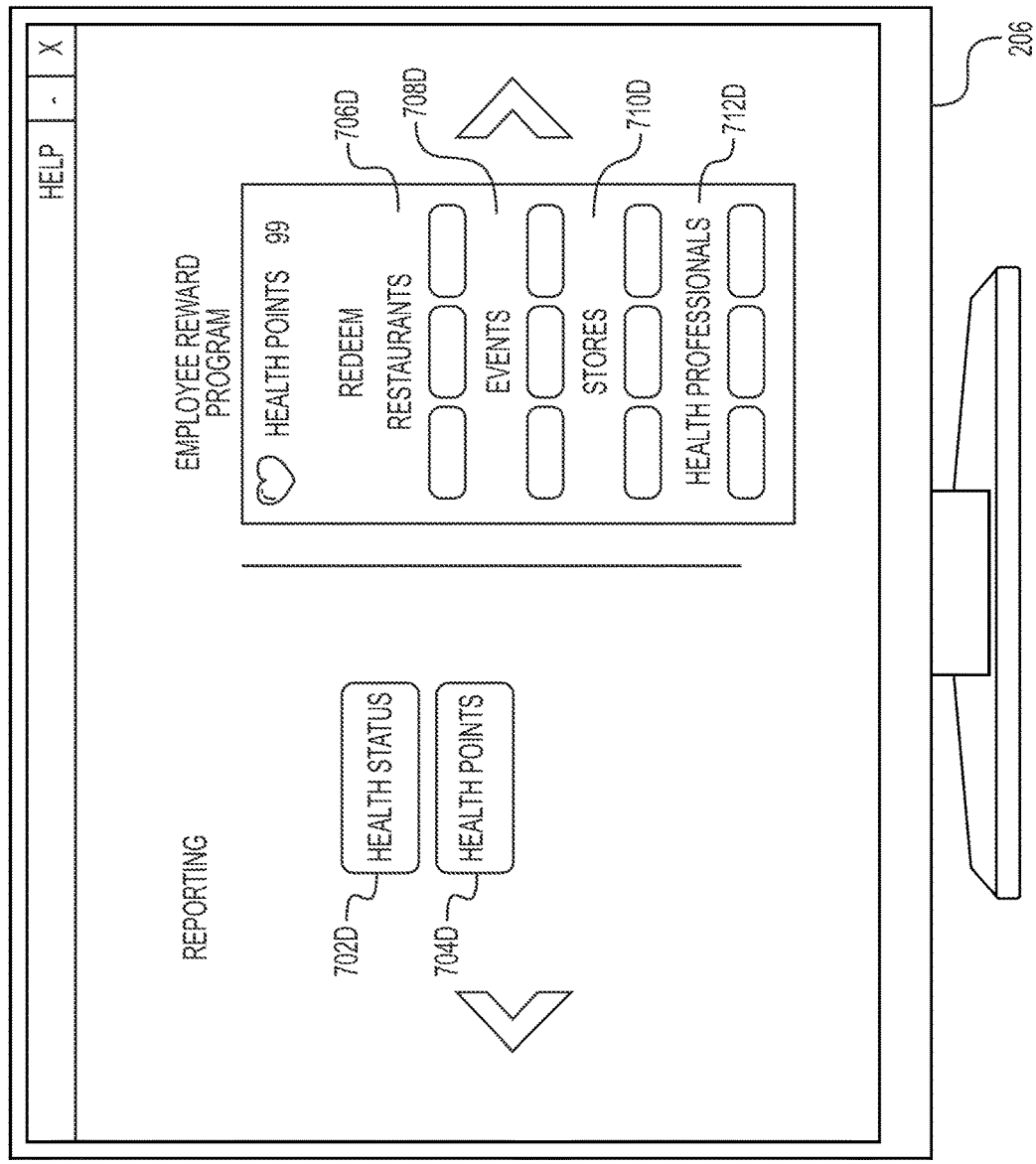

FIG. 7D depicts an example screenshot of a display 206 of a user interface 208 that enables a user to view information received or accumulated over the course of a session. For example, a user may be able to view data received from various sensors at one or more points of the workout (e.g., by selecting "health status" 702D). The controller 202 of the interactive workstation 104 may evaluate and re-evaluate received biometric or values on a daily, weekly or monthly basis and can modify, create or recommend sessions for users in order to help improve the users' lifestyle and make users healthier, specific to their needs. In some embodiments, as illustrated in 704D of FIG. 7D, users may be able to accumulate points based on, for example, completing sessions successfully, or progressing through sessions. Various users, who may each use interactive workstations 104 may interact with one another if they choose to do so. The interaction and gamification (via the accumulated points) may allow internal competitions to occur, thereby challenging individuals to improve their health and wellness. As a result of accumulating points, users may be rewarded, for example, by enabling users to redeem their points at restaurants 706D, events 708D, stores 710D, and/or visits to health professionals 712D.

These and other embodiments of the systems and methods may be used as would be recognized by those skilled in the art. The above descriptions of various systems and methods are intended to illustrate specific examples and describe certain ways of making and using the systems disclosed and described here. These descriptions are neither intended to be nor should be taken as an exhaustive list of the possible ways in which these systems can be made and used. A number of modifications, including substitutions of systems between or among examples and variations among combinations can be made. Any feature of any example described herein may be combined with any other feature of other examples. Those modifications and variations should be apparent to those of ordinary skill in this area after having read this disclosure.

What is claimed is:

1. A method of moving a tabletop of a workstation in a plurality of dimensions based on biometric input associated with a user, the method being performed by a controller that is configured to send control signals to one or more actuators to move the tabletop, wherein the controller is connected to one or more user devices having a user interface, the method comprising:

accessing a user profile associated with or stored in a user device of the one or more user devices;

determining one or more parameters for moving the tabletop, based on the user profile, for eliciting one or more desired biometric inputs from the user that indicate the health of the user or movement by the user at one or more times during the movement of the tabletop; and repeating one or more iterations of:
moving the tabletop based on the one or more parameters, by sending control signals from the controller to the one or more actuators;
receiving, into a data storage device, one or more actual biometric inputs from the user indicating the health of the user or movement by the user;
determining whether the one or more parameters for moving the tabletop elicit the one or more desired biometric inputs by comparing the received one or more actual biometric inputs with the one or more desired biometric inputs; and
if the one or more parameters do not elicit the one or more desired biometric inputs, adjusting the one or more parameters, wherein the one or more actual biometric inputs of the user include one or more of:
a blood pressure;
a respiratory rate;
a measurement of oxygen saturation;
a glucose concentration;
a measurement of perspiration; and
a brain activity measurement.

2. The method of claim 1, further comprising:
displaying information related to the received one or more actual biometric inputs on the user interface of the one or more user devices.

3. The method of claim 1, wherein if one or more parameters do not elicit the one or more desired biometric inputs, adjusting the one or more parameters includes:
enabling a user of the one or more user devices to adjust the one or more parameters; and
receiving input from the user of the one or more user devices for adjusting the one or more parameters.

4. The method of claim 1, wherein if the one or more parameters do not elicit the desired biometric inputs, adjusting the one or more parameters includes:
receiving information on previous configurations of parameters that elicited the desired biometric inputs; and reconfiguring the one or more parameters to conform with the previous configurations of the parameters.

5. The method of claim 1, wherein a user of the one or more user devices includes, one or more of:
the user from whom biometric input is received;
a health professional of the user from whom biometric input is received;
an insurance provider of the user from whom biometric input is received;
an employer, colleague, or manager of the user from whom biometric input is received; or
any third party that has been authorized by the user biometric input is received to receive information related to the user from whom biometric input is received.

6. The method of claim 1, wherein the one or more actual biometric inputs of the user include one or more of:
a respiratory rate;
a measurement of oxygen saturation;
a measurement of perspiration; and
a brain activity measurement.

7. The method of claim 1, wherein repeating one or more iterations further comprises:
receiving one or more measurements of the performance or efficiency of the workstation; and
determining whether the one or more measurements of the performance or efficiency falls above or below a predetermined threshold.

8. The method of claim 7, wherein the one or more measurements of the performance or efficiency of the workstation includes one or more of:
a measurement of the revolutions, frequency, or speed of moving parts of the workstation;
a measurement of a strength of connectivity with the one or more user devices, the one or more actuators, any one or more sensors, or any one or more peripheral devices;
a measurement of a current of the electrical parts; and
a measurement of a position of one or more parts of the workstation.

9. The method of claim 7, wherein, if one or more measurements of the performance or efficiency falls above or below a predetermined threshold, performing one or more of:
reconfiguring one or more parameters for moving the tabletop; or
displaying, on the user interface of the one or more user devices, information related to the one or more measurements of the performance or efficiency falling above or below a predetermined threshold.

10. The method of claim 1, wherein the user profile information includes one or more of:
biographical information identifying the user;
demographic information regarding the user;
anthropometric measurements of the user;
measurements of one or more parts of the workstation;
physical or physiological information of the user;
pre-existing health conditions of the user;
contact information of a health professional, therapist, employer, or insurance provider of the user; or
goals of the user related to the movement of the tabletop.

11. The method of claim 1, wherein the one or more parameters for moving the tabletop include one or more of a periodicity, a speed, a range, a duration, and a type of motion for the tabletop of the interactive workstation, with respect to the user position.

12. The method of claim 1, wherein the controller is further connected to one or more other controllers, wherein the one or more other controllers perform methods of moving a tabletop of one or more other workstations in a plurality of dimensions based on biometric input associated with one or more other users, and wherein the controller is configured to display information related to one or more actual biometric inputs of the one or more other users.

13. A system for moving a tabletop of a workstation in a plurality of dimensions based on biometric input associated with a user, the system comprising:

a data storage device storing biometric input and instructions for moving the tabletop of the workstation in the plurality of dimensions based on the biometric input;

one or more user devices having a user interface enabling a user of the system to create or access a user profile;

the workstation having the tabletop and one or more actuators configured to move the tabletop;

a controller having at least one processor configured to:
  accessing the user profile associated with or stored in a user device of the one or more user devices;
  determining one or more parameters for moving the tabletop, based on the user profile, for eliciting one or more desired biometric inputs from the user that indicate the health of the user or movement by the user at one or more times during the movement of the tabletop; and
  repeating one or more iterations of:
    moving the tabletop based on the one or more parameters, by sending control signals from the controller to the one or more actuators of the tabletop;
    receiving, into the data storage device, one or more actual biometric inputs from the user indicating the health of the user or movement by the user;
    determining whether the one or more parameters for moving the tabletop elicit the one or more desired biometric inputs by comparing the received one or more actual biometric inputs with the one or more desired biometric inputs; and
    if the one or more parameters do not elicit the one or more desired biometric inputs, adjusting the one or more parameters, wherein the one or more actual biometric inputs of the user include one or more of:
  a blood pressure;
  a respiratory rate;
  a measurement of oxygen saturation;
  a glucose concentration;
  a measurement of perspiration; and
  a brain activity measurement.

14. The system of claim 13, further comprising one or more sensors for receiving biometric input from the user and transmitting the biometric input to the data storage device.

15. The system of claim 13, wherein the controller is further configured for:
  displaying information related to the received one or more actual biometric inputs on the user interface of one or more user devices.

16. The system of claim 13, wherein if one or more parameters do not elicit the one or more desired biometric inputs, adjusting the one or more parameters includes:
  enabling a user of the one or more user devices to adjust the one or more parameters; and
  receiving input from the user of the one or more user devices for adjusting one or more parameters.

17. The system of claim 13, wherein if one or more parameters do not elicit the one or more desired biometric inputs, adjusting the one or more parameters includes:
  receiving information on previous configurations of parameters that elicited the one or more desired biometric inputs;
  and reconfiguring the one or more parameters to conform with the previous configurations of the parameters.

18. The system of claim 13, wherein repeating one or more iterations further comprises:

receiving one or more measurements of the performance or efficiency of the workstation; and
  determining whether the one or more measurements of the performance or efficiency falls above or below a predetermined threshold.

19. The system of claim 13, wherein the one or more actual biometric inputs of the user include one or more of:
  a respiratory rate;
  a measurement of oxygen saturation;
  a measurement of perspiration; and
  a brain activity measurement.

20. A non-transitory computer readable medium for use on a computer system containing computer-executable programming instructions that, when executed by a processor, cause the processor to perform a method for moving a tabletop of a workstation in a plurality of dimensions based on biometric input associated with a user, wherein the processor is connected to one or more user devices having a user interface and one or more actuators of the workstation, the method comprising:
  accessing a user profile associated with or stored in a user device of the one or more user devices;
  determining one or more parameters for moving the tabletop, based on the user profile, for eliciting one or more desired biometric inputs from the user that indicate the health of the user or movement by the user at one or more times during the movement of the tabletop; and
  repeating one or more iterations of:
    moving the tabletop based on the one or more parameters, by sending control signals to the one or more actuators;
    receiving, into a data storage device, one or more actual biometric inputs from the user indicating the health of the user or movement by the user;
    determining whether the one or more parameters for moving the tabletop elicit the one or more desired biometric inputs by comparing the received one or more actual biometric inputs with the one or more desired biometric inputs; and
    if the one or more parameters do not elicit the one or more desired biometric inputs, adjusting the one or more parameters, wherein the one or more actual biometric inputs of the user include one or more of:
  a blood pressure;
  a respiratory rate;
  a measurement of oxygen saturation;
  a glucose concentration;
  a measurement of perspiration; and
  a brain activity measurement.

21. The computer readable medium of claim 20, further comprising:
  displaying information related to the received one or more actual biometric inputs on the user interface of one or more user devices.
  a brain activity measurement.

22. The computer readable medium of claim 20, wherein the one or more actual biometric inputs of the user include one or more of:
  a respiratory rate;
  a measurement of oxygen saturation;
  a measurement of perspiration; and
  a brain activity measurement.

* * * * *